US012797201B2

(12) United States Patent
Penner et al.

(10) Patent No.: US 12,797,201 B2
(45) Date of Patent: Nov. 17, 2026

(54) COUPLING SYSTEMS AND METHODS

(71) Applicant: WRIGHT MEDICAL TECHNOLOGY, INC., Memphis, TN (US)

(72) Inventors: Murray J. Penner, Vancouver (CA); Ramon Luna, Arlington, TN (US); Johnny McGee, Halls, TN (US); Jesse G. Moore, Germantown, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 512 days.

(21) Appl. No.: 18/348,513

(22) Filed: Jul. 7, 2023

(65) Prior Publication Data

US 2024/0115392 A1 Apr. 11, 2024

Related U.S. Application Data

(60) Provisional application No. 63/378,714, filed on Oct. 7, 2022.

(51) Int. Cl.

*A61F 2/30* (2006.01)
*A61F 2/38* (2006.01)
*A61F 2/46* (2006.01)

(52) U.S. Cl.

CPC .............. *A61F 2/389* (2013.01); *A61F 2/461* (2013.01); *A61F 2002/30383* (2013.01);

(Continued)

(58) Field of Classification Search

CPC ............................................ A61F 2002/30329

See application file for complete search history.

(56) References Cited

U.S. PATENT DOCUMENTS 3,314,420 A 4/1967 Smith et al.
3,605,123 A 9/1971 Hahn (Continued)

FOREIGN PATENT DOCUMENTS

CN 1662186 8/2005
CN 101111197 1/2008

(Continued)

OTHER PUBLICATIONS

Andersson, et al., “Macintosh Arthroplasty In Rheumatoid Arthritis,” Acta. Orthrop. Scand., 1974, pp. 245-259, 45(2).

(Continued)

*Primary Examiner* — Jacqueline Woznicki

(74) *Attorney, Agent, or Firm* — DUANE MORRIS LLP

(57) ABSTRACT

Various systems and methods are disclosed for joining at least two components of a prosthesis. For example, a system may include a first component having a first a first body extending from a first face to a second face. An engagement element may be disposed on the first face of the first body and may be configured to engage a second component. A biasing member may be disposed on the engagement element and may be configured to latch a second component to the first component. A securing mechanism may be configured to receive a locking mechanism at an angle with respect to a longitudinal axis. The locking mechanism may be adapted to interact with the biasing member.

12 Claims, 28 Drawing Sheets

(52) U.S. Cl.
CPC ............... *A61F 2002/30387* (2013.01); *A61F 2002/30476* (2013.01); *A61F 2002/30481* (2013.01); *A61F 2002/30484* (2013.01); *A61F 2002/30485* (2013.01); *A61F 2002/30492* (2013.01); *A61F 2002/30494* (2013.01); *A61F 2002/305* (2013.01); *A61F 2002/30505* (2013.01); *A61F 2002/30507* (2013.01); *A61F 2002/30515* (2013.01); *A61F 2002/4619* (2013.01); *A61F 2220/0041* (2013.01)

(56) References Cited

U.S. PATENT DOCUMENTS 3,708,883 A 1/1973 Flander
3,798,679 A 3/1974 Ewald
3,808,606 A 5/1974 Tronzo
3,843,975 A 10/1974 Tronzo
3,855,638 A 12/1974 Pilliar
3,938,198 A 2/1976 Kahn et al.
3,987,499 A 10/1976 Scharbach et al.
4,052,753 A 10/1977 Dedo
4,055,862 A 11/1977 Farling
4,085,466 A 4/1978 Goodfellow et al.
4,098,626 A 7/1978 Graham et al.
4,203,444 A 5/1980 Bonnell et al.
4,213,816 A 7/1980 Morris
4,257,129 A * 3/1981 Volz ........................ A61F 2/389 623/20.33
4,340,978 A 7/1982 Buechel et al.
4,368,040 A 1/1983 Weissman
4,436,684 A 3/1984 White
4,501,266 A 2/1985 McDaniel
4,502,161 A 3/1985 Wall
4,578,806 A 3/1986 Grass et al.
4,586,496 A 5/1986 Keller
4,594,380 A 6/1986 Chapin et al.
4,601,290 A 7/1986 Effron et al.
4,609,551 A 9/1986 Caplan et al.
4,627,853 A 12/1986 Campbell et al.
4,703,751 A 11/1987 Pohl
4,704,686 A 11/1987 Aldinger
4,715,860 A 12/1987 Amstutz et al.
4,721,104 A 1/1988 Kaufman et al.
4,759,350 A 7/1988 Dunn et al.
4,769,040 A 9/1988 Wevers
4,841,975 A 6/1989 Woolson
4,846,835 A 7/1989 Grande
4,865,607 A 9/1989 Witzel et al.
4,880,429 A 11/1989 Stone
4,936,862 A 6/1990 Walker et al.
4,979,949 A 12/1990 Matsen, III et al.
5,002,547 A 3/1991 Poggie
5,041,138 A 8/1991 Vacanti et al.
5,059,216 A 10/1991 Winters
5,067,964 A 11/1991 Richmond et al.
5,108,442 A * 4/1992 Smith ..................... A61F 2/389 623/20.33
5,122,144 A 6/1992 Bert et al.
5,129,908 A 7/1992 Petersen
5,133,759 A 7/1992 Turner
5,154,717 A 10/1992 Matsen, III et al.
5,162,430 A 11/1992 Rhee et al.
5,171,322 A 12/1992 Kenny
5,197,985 A 3/1993 Caplan et al.
5,206,023 A 4/1993 Hunziker
5,226,914 A 7/1993 Caplan et al.
5,234,433 A 8/1993 Bert et al.
5,250,050 A 10/1993 Poggie et al.
5,258,032 A 11/1993 Bertin
5,270,300 A 12/1993 Hunziker
5,288,797 A 2/1994 Khalil et al.
5,303,148 A 4/1994 Mattson et al.
5,306,311 A 4/1994 Stone et al.
5,314,482 A 5/1994 Goodfellow et al.
5,344,459 A 9/1994 Swartz
5,360,446 A 11/1994 Kennedy
5,365,996 A 11/1994 Crook
5,368,858 A 11/1994 Hunziker
5,370,692 A 12/1994 Fink et al.
5,380,332 A 1/1995 Ferrante
5,387,216 A 2/1995 Thornhill et al.
5,454,816 A 10/1995 Ashby
5,462,550 A 10/1995 Dietz et al.
5,468,787 A 11/1995 Braden et al.
5,474,559 A 12/1995 Bertin et al.
5,478,739 A 12/1995 Slivka et al.
5,486,180 A 1/1996 Dietz et al.
5,501,687 A 3/1996 Willert et al.
5,503,162 A 4/1996 Athanasiou et al.
5,520,695 A 5/1996 Luckman
5,523,843 A 6/1996 Yamane et al.
5,540,696 A 7/1996 Booth, Jr. et al.
5,542,947 A 8/1996 Treacy
5,554,190 A 9/1996 Draenert
5,556,432 A 9/1996 Kubein-Meesenburg et al.
5,571,205 A 11/1996 James
5,575,793 A 11/1996 Carls et al.
5,578,037 A 11/1996 Sanders et al.
5,593,450 A 1/1997 Scott et al.
5,597,379 A 1/1997 Haines et al.
5,601,563 A 2/1997 Burke et al.
5,613,970 A 3/1997 Houston et al.
5,616,146 A 4/1997 Murray
5,630,820 A 5/1997 Todd
5,632,745 A 5/1997 Schwartz
5,645,604 A 7/1997 Schneider et al.
5,649,929 A 7/1997 Callaway
5,658,290 A 8/1997 Techeira
5,671,741 A 9/1997 Lang et al.
5,682,886 A 11/1997 Delp et al.
5,683,466 A 11/1997 Vitale
5,684,562 A 11/1997 Fujieda
5,688,282 A 11/1997 Baron et al.
5,728,162 A 3/1998 Eckhoff
5,735,277 A 4/1998 Schuster
5,749,874 A 5/1998 Schwartz
5,749,876 A 5/1998 Duvillier et al.
5,765,561 A 6/1998 Chen et al.
5,768,134 A 6/1998 Swaelens et al.
5,769,899 A 6/1998 Schwartz et al.
5,782,842 A 7/1998 Kloess et al.
5,786,217 A 7/1998 Tuba et al.
5,798,924 A 8/1998 Eufinger et al.
5,800,438 A 9/1998 Tuke et al.
5,824,083 A 10/1998 Draenert
5,827,289 A 10/1998 Reiley et al.
5,830,216 A 11/1998 Insall et al.
5,835,619 A 11/1998 Morimoto et al.
5,842,477 A 12/1998 Naughton et al.
5,847,804 A 12/1998 Sarver et al.
5,853,746 A 12/1998 Hunziker
5,860,981 A 1/1999 Bertin et al.
5,871,018 A 2/1999 Delp et al.
5,871,542 A 2/1999 Goodfellow et al.
5,871,546 A 2/1999 Colleran et al.
5,879,390 A 3/1999 Kubein-Meesenburg et al.
5,880,976 A 3/1999 DiGioia, III et al.
5,885,296 A 3/1999 Masini
5,885,297 A 3/1999 Matsen, III
5,885,298 A 3/1999 Herrington et al.
5,897,559 A 4/1999 Masini
5,899,859 A 5/1999 Votruba et al.
5,900,245 A 5/1999 Sawhney et al.
5,906,934 A 5/1999 Grande et al.
5,911,723 A 6/1999 Ashby et al.
5,916,220 A 6/1999 Masini
5,939,323 A 8/1999 Valentini et al.
5,951,475 A 9/1999 Gueziec et al.
5,961,523 A 10/1999 Masini
5,968,051 A 10/1999 Luckman et al.
5,972,385 A 10/1999 Liu et al.
5,995,738 A 11/1999 DiGioia, III et al.
6,001,895 A 12/1999 Harvey et al.
6,002,859 A 12/1999 DiGioia, III et al.

(56) References Cited

U.S. PATENT DOCUMENTS 6,006,126 A 12/1999 Cosman
6,007,537 A 12/1999 Burkinshaw et al.
6,010,509 A 1/2000 Delgado et al.
6,013,081 A 1/2000 Burkinshaw et al.
6,013,103 A 1/2000 Kaufman et al.
6,046,379 A 4/2000 Stone et al.
6,056,754 A 5/2000 Haines et al.
6,056,756 A 5/2000 Eng et al.
6,057,927 A 5/2000 Levesque et al.
6,077,270 A 6/2000 Katz
6,082,364 A 7/2000 Balian et al.
6,090,144 A 7/2000 Letot et al.
6,093,204 A 7/2000 Stone
6,096,043 A 8/2000 Techiera et al.
6,102,916 A 8/2000 Masini
6,106,529 A 8/2000 Techiera
6,110,209 A 8/2000 Stone
6,120,541 A 9/2000 Johnson
6,126,690 A 10/2000 Ateshian et al.
6,139,578 A 10/2000 Lee et al.
6,156,069 A 12/2000 Amstutz
6,161,080 A 12/2000 Aouni-Ateshian et al.
6,187,010 B1 2/2001 Masini
6,200,606 B1 3/2001 Peterson et al.
6,203,546 B1 3/2001 MacMahon
6,203,576 B1 3/2001 Afriat et al.
6,205,411 B1 3/2001 DiGioia, III et al.
6,206,927 B1 3/2001 Fell et al.
6,214,369 B1 4/2001 Grande et al.
6,217,894 B1 4/2001 Sawhney et al.
6,219,571 B1 4/2001 Hargreaves et al.
6,224,632 B1 5/2001 Pappas et al.
6,235,060 B1 5/2001 Kubein-Meesenburg et al.
6,251,143 B1 6/2001 Schwartz et al.
6,254,639 B1 7/2001 Peckitt
6,277,151 B1 8/2001 Lee et al.
6,280,476 B1 * 8/2001 Metzger .................... A61F 2/34 623/18.11
6,281,195 B1 8/2001 Rueger et al.
6,283,980 B1 9/2001 Vibe-Hansen et al.
6,296,646 B1 10/2001 Williamson
6,299,905 B1 10/2001 Peterson et al.
6,322,588 B1 11/2001 Ogle et al.
6,327,491 B1 12/2001 Franklin et al.
6,328,765 B1 12/2001 Hardwick et al.
6,344,043 B1 2/2002 Pappas
6,344,059 B1 2/2002 Krakovits et al.
6,352,558 B1 3/2002 Spector
6,358,253 B1 3/2002 Torrie et al.
6,365,405 B1 4/2002 Salzmann et al.
6,371,958 B1 4/2002 Overaker
6,373,250 B1 4/2002 Tsoref et al.
6,375,658 B1 4/2002 Hangody et al.
6,379,367 B1 4/2002 Vibe-Hansen et al.
6,382,028 B1 5/2002 Wooh et al.
6,383,228 B1 5/2002 Schmotzer
6,387,131 B1 5/2002 Miehlke et al.
6,409,767 B1 6/2002 Perice et al.
6,429,013 B1 8/2002 Halvorsen et al.
6,443,988 B2 9/2002 Felt et al.
6,443,991 B1 9/2002 Running
6,444,222 B1 9/2002 Asculai et al.
6,459,927 B1 10/2002 Franklin et al.
6,459,948 B1 10/2002 Ateshian et al.
6,468,314 B2 10/2002 Schwartz et al.
6,478,799 B1 11/2002 Williamson
6,479,996 B1 11/2002 Hoogeveen et al.
6,510,334 B1 1/2003 Schuster et al.
6,520,964 B2 2/2003 Tallarida et al.
6,558,421 B1 5/2003 Fell et al.
6,560,476 B1 5/2003 Pelletier et al.
6,575,980 B1 6/2003 Robie et al.
6,620,168 B1 9/2003 Lombardo et al.
6,626,945 B2 9/2003 Simon et al.
6,626,948 B2 9/2003 Storer et al.
6,632,225 B2 10/2003 Sanford et al.
6,632,235 B2 10/2003 Weikel et al.
6,652,587 B2 11/2003 Felt et al.
6,673,077 B1 1/2004 Katz
6,679,917 B2 1/2004 Ek
6,712,856 B1 3/2004 Carignan et al.
6,738,657 B1 5/2004 Franklin et al.
6,905,514 B2 6/2005 Carignan et al.
6,916,341 B2 7/2005 Rolston
6,928,742 B2 8/2005 Broers et al.
6,932,842 B1 8/2005 Litschko et al.
6,942,667 B1 9/2005 Song
6,944,518 B2 9/2005 Roose
6,969,393 B2 11/2005 Pinczewski et al.
6,980,849 B2 12/2005 Sasso
6,988,015 B1 1/2006 Schopf et al.
6,993,374 B2 1/2006 Sasso
7,008,430 B2 3/2006 Dong et al.
7,058,439 B2 6/2006 Eaton et al.
7,060,074 B2 6/2006 Rosa et al.
7,104,997 B2 9/2006 Lionberger et al.
7,115,131 B2 10/2006 Engh et al.
7,117,027 B2 10/2006 Zheng et al.
7,125,423 B2 * 10/2006 Hazebrouck ........ A61F 2/30721 606/62
7,141,053 B2 11/2006 Rosa et al.
7,184,814 B2 2/2007 Lang et al.
7,201,762 B2 4/2007 Green, Jr. et al.
7,217,276 B2 5/2007 Henderson et al.
7,239,908 B1 7/2007 Alexander et al.
7,245,697 B2 7/2007 Lang
7,282,054 B2 10/2007 Steffensmeier et al.
7,292,674 B2 11/2007 Lang
7,347,690 B2 3/2008 Jordan et al.
7,364,581 B2 4/2008 Michalowicz
7,377,924 B2 5/2008 Raistrick et al.
7,379,529 B2 5/2008 Lang
7,467,892 B2 12/2008 Lang et al.
7,468,075 B2 12/2008 Lang et al.
7,534,246 B2 5/2009 Reiley et al.
7,534,263 B2 5/2009 Burdulis, Jr. et al.
7,618,451 B2 11/2009 Berez et al.
7,641,698 B1 * 1/2010 Gibbs .................. A61F 2/4637 623/22.15
7,747,305 B2 6/2010 Dean et al.
7,806,896 B1 10/2010 Bonutti
7,881,768 B2 2/2011 Lang et al.
7,981,158 B2 7/2011 Fitz et al.
7,983,777 B2 7/2011 Melton et al.
8,036,729 B2 10/2011 Lang et al.
8,062,302 B2 11/2011 Lang et al.
8,066,708 B2 11/2011 Lang et al.
8,083,745 B2 12/2011 Lang et al.
8,105,330 B2 1/2012 Fitz et al.
8,112,142 B2 2/2012 Alexander et al.
8,122,592 B2 2/2012 Burdulis, Jr. et al.
RE43,282 E 3/2012 Alexander et al.
8,496,663 B2 7/2013 White et al.
8,535,319 B2 9/2013 Ball
8,579,980 B2 11/2013 Delurio et al.
8,715,362 B2 5/2014 Reiley et al.
8,808,297 B2 8/2014 Stemniski
8,808,303 B2 8/2014 Stemniski
9,017,334 B2 4/2015 Carroll et al.
9,125,674 B2 9/2015 White et al.
9,265,511 B2 2/2016 White et al.
9,402,640 B2 8/2016 Stemniski et al.
9,672,607 B2 6/2017 Demri et al.
10,105,168 B2 10/2018 Blau
10,130,430 B2 11/2018 Kao et al.
10,390,842 B2 8/2019 Sander
10,413,308 B2 9/2019 Stemniski et al.
10,433,911 B2 10/2019 Wang et al.
10,456,179 B2 10/2019 Luna et al.
10,667,867 B2 6/2020 Ashish et al.
10,835,265 B2 11/2020 White et al.
10,835,266 B2 11/2020 White et al.
11,147,627 B2 10/2021 Gangwar et al.
11,172,945 B1 11/2021 Lian

(56) References Cited

U.S. PATENT DOCUMENTS

2001/0001120 A1 5/2001 Masini
2001/0010023 A1 7/2001 Schwartz et al.
2001/0039455 A1 11/2001 Simon et al.
2002/0013626 A1 1/2002 Geisllich et al.
2002/0029038 A1 3/2002 Haines
2002/0045940 A1 4/2002 Giannelli et al.
2002/0059049 A1 5/2002 Bradbury et al.
2002/0068979 A1 6/2002 Brown et al.
2002/0072821 A1 6/2002 Baker
2002/0079601 A1 6/2002 Russell et al.
2002/0082703 A1 6/2002 Repicci
2002/0087274 A1 7/2002 Alexander et al.
2002/0106625 A1 8/2002 Hung et al.
2002/0115647 A1 8/2002 Halvorsen et al.
2002/0120274 A1 8/2002 Overaker et al.
2002/0120281 A1 8/2002 Overaker
2002/0123817 A1 9/2002 Clasbrummel et al.
2002/0127264 A1 9/2002 Felt et al.
2002/0133230 A1 9/2002 Repicci
2002/0143402 A1 10/2002 Steinberg
2002/0151986 A1 10/2002 Asculai et al.
2002/0156150 A1 10/2002 Asculai et al.
2002/0156479 A1 10/2002 Schulzki et al.
2002/0173852 A1 11/2002 Felt et al.
2002/0183850 A1 12/2002 Felt et al.
2002/0198531 A1 12/2002 Millard et al.
2003/0028196 A1 2/2003 Bonutti
2003/0055500 A1 3/2003 Fell et al.
2003/0055501 A1 3/2003 Fell et al.
2003/0055502 A1 3/2003 Lang et al.
2003/0060882 A1 3/2003 Fell et al.
2003/0060883 A1 3/2003 Fell et al.
2003/0060884 A1 3/2003 Fell et al.
2003/0060885 A1 3/2003 Fell et al.
2003/0100907 A1 5/2003 Rosa et al.
2003/0100953 A1 5/2003 Rosa et al.
2003/0120347 A1 6/2003 Steinberg
2003/0158558 A1 8/2003 Horn
2003/0158606 A1 8/2003 Coon et al.
2003/0163137 A1 8/2003 Smucker et al.
2003/0173695 A1 9/2003 Monkhouse et al.
2003/0216669 A1 11/2003 Lang et al.
2003/0225457 A1 12/2003 Justin et al.
2003/0236521 A1 12/2003 Brown et al.
2003/0236526 A1 12/2003 Van Hoeck et al.
2004/0098133 A1 5/2004 Carignan et al.
2004/0102852 A1 5/2004 Johnson et al.
2004/0122521 A1 6/2004 Lee et al.
2004/0133276 A1 7/2004 Lang et al.
2004/0138754 A1 7/2004 Lang et al.
2004/0147927 A1 7/2004 Tsougarakis et al.
2004/0153079 A1 8/2004 Tsougarakis et al.
2004/0153162 A1 8/2004 Sanford et al.
2004/0153164 A1 8/2004 Sanford et al.
2004/0167390 A1 8/2004 Alexander et al.
2004/0167630 A1 8/2004 Rolston
2004/0193268 A1 9/2004 Hazebrouck et al.
2004/0193280 A1 9/2004 Webster et al.
2004/0199166 A1 10/2004 Schmieding et al.
2004/0204644 A1 10/2004 Tsougarakis et al.
2004/0204760 A1 10/2004 Fitz et al.
2004/0236424 A1 11/2004 Berez et al.
2004/0249386 A1 12/2004 Faoro
2005/0015153 A1 1/2005 Goble et al.
2005/0021039 A1 1/2005 Cusick et al.
2005/0043807 A1 2/2005 Wood
2005/0049603 A1 3/2005 Calton et al.
2005/0055028 A1 3/2005 Haines
2005/0085920 A1 4/2005 Williamson
2005/0107883 A1 5/2005 Goodfried et al.
2005/0107884 A1 5/2005 Johnson et al.
2005/0119664 A1 6/2005 Carignan et al.
2005/0143745 A1 6/2005 Hodorek et al.
2005/0148843 A1 7/2005 Roose
2005/0171545 A1 8/2005 Walsh et al.
2005/0171612 A1 8/2005 Rolston
2005/0192588 A1 9/2005 Garcia
2005/0216305 A1 9/2005 Funderud
2005/0234461 A1 10/2005 Burdulis, Jr. et al.
2005/0267584 A1 12/2005 Burdulis et al.
2006/0052795 A1 3/2006 Burdulis et al.
2006/0111722 A1 5/2006 Bouadi
2006/0149283 A1 7/2006 May et al.
2006/0200162 A1 9/2006 Farling et al.
2006/0229730 A1* 10/2006 Railey .................... A61B 17/15
623/23.44
2006/0235421 A1 10/2006 Rosa et al.
2007/0015995 A1 1/2007 Lang
2007/0073305 A1 3/2007 Lionberger et al.
2007/0118141 A1 5/2007 Marchyn et al.
2007/0150065 A1 6/2007 Angibaud
2007/0162025 A1 7/2007 Tornier et al.
2007/0198022 A1 8/2007 Lang et al.
2007/0203430 A1 8/2007 Lang et al.
2007/0203455 A1 8/2007 Tremaglio et al.
2007/0233128 A1 10/2007 Schmieding et al.
2007/0233151 A1 10/2007 Chudik
2007/0233156 A1 10/2007 Metzger
2007/0276224 A1 11/2007 Lang et al.
2007/0293868 A1 12/2007 Delfosse et al.
2008/0004709 A1 1/2008 O'Neill et al.
2008/0015433 A1 1/2008 Alexander et al.
2008/0025463 A1 1/2008 Lang et al.
2008/0031412 A1 2/2008 Delfosse et al.
2008/0058613 A1 3/2008 Lang et al.
2008/0058945 A1 3/2008 Hajaj et al.
2008/0114370 A1 5/2008 Schoenefeld
2008/0170659 A1 7/2008 Lang et al.
2008/0195109 A1 8/2008 Hunter et al.
2008/0195216 A1 8/2008 Lang
2008/0219412 A1 9/2008 Lang
2008/0243127 A1 10/2008 Lang
2008/0255565 A1 10/2008 Fletcher
2008/0275452 A1 11/2008 Lang et al.
2008/0281328 A1 11/2008 Lang et al.
2008/0281329 A1 11/2008 Lang et al.
2008/0281426 A1 11/2008 Fitz et al.
2008/0287953 A1 11/2008 Sers
2008/0288079 A1 11/2008 Leibel
2009/0024131 A1 1/2009 Metzger et al.
2009/0043310 A1 2/2009 Rasmussen
2009/0076371 A1 3/2009 Lang et al.
2009/0087276 A1 4/2009 Rose
2009/0088753 A1 4/2009 Aram et al.
2009/0088758 A1 4/2009 Bennett
2009/0099567 A1 4/2009 Zajac
2009/0131941 A1 5/2009 Park et al.
2009/0131942 A1 5/2009 Aker et al.
2009/0149964 A1 6/2009 May et al.
2009/0198244 A1 8/2009 Libel
2009/0198337 A1* 8/2009 Phan ..................... A61F 2/4657
623/17.11
2009/0204115 A1 8/2009 Dees et al.
2009/0222014 A1 9/2009 Bojarski et al.
2009/0307893 A1 12/2009 Bojarski et al.
2010/0016970 A1* 1/2010 Kapitan .................. A61F 2/442
606/246
2010/0076441 A1 3/2010 May et al.
2010/0160917 A1 6/2010 Fitz et al.
2010/0262150 A1 10/2010 Lian
2010/0274251 A1 10/2010 Ranft
2010/0281678 A1 11/2010 Burdulis, Jr. et al.
2010/0298894 A1 11/2010 Bojarski et al.
2010/0305573 A1 12/2010 Fitz et al.
2010/0305574 A1 12/2010 Fitz et al.
2011/0066193 A1 3/2011 Lang et al.
2011/0071581 A1 3/2011 Lang et al.
2011/0137422 A1 6/2011 Wilkes
2011/0213368 A1 9/2011 Fitz et al.
2011/0213373 A1 9/2011 Fitz et al.
2011/0213374 A1 9/2011 Fitz et al.
2011/0213377 A1 9/2011 Lang et al.
2011/0213427 A1 9/2011 Fitz et al.
2011/0213428 A1 9/2011 Fitz et al.

(56) References Cited

U.S. PATENT DOCUMENTS

| | | | | |
|---|---|---|---|---|
| 2011/0213429 | A1 | 9/2011 | Lang et al. | |
| 2011/0213430 | A1 | 9/2011 | Lang et al. | |
| 2011/0213431 | A1 | 9/2011 | Fitz et al. | |
| 2011/0218539 | A1 | 9/2011 | Fitz et al. | |
| 2011/0218542 | A1 | 9/2011 | Lian et al. | |
| 2011/0218584 | A1 | 9/2011 | Fitz et al. | |
| 2011/0230888 | A1 | 9/2011 | Lang et al. | |
| 2011/0238073 | A1 | 9/2011 | Lang et al. | |
| 2011/0313423 | A1 | 12/2011 | Lang et al. | |
| 2011/0319897 | A1 | 12/2011 | Lang et al. | |
| 2011/0319900 | A1 | 12/2011 | Lang et al. | |
| 2012/0029520 | A1 | 2/2012 | Lang et al. | |
| 2012/0041446 | A1 | 2/2012 | Wong et al. | |
| 2012/0066892 | A1 | 3/2012 | Lang et al. | |
| 2012/0071881 | A1 | 3/2012 | Lang et al. | |
| 2012/0071882 | A1 | 3/2012 | Lang et al. | |
| 2012/0071883 | A1 | 3/2012 | Lang et al. | |
| 2012/0072185 | A1 | 3/2012 | Lang et al. | |
| 2012/0083892 | A1 | 4/2012 | Kehres et al. | |
| 2012/0101503 | A1 | 4/2012 | Lang et al. | |
| 2012/0143197 | A1 | 6/2012 | Lang et al. | |
| 2012/0151730 | A1 | 6/2012 | Fitz et al. | |
| 2012/0158001 | A1 | 6/2012 | Burdulis, Jr. et al. | |
| 2013/0261628 | A1 | 10/2013 | Burley et al. | |
| 2014/0270065 | A1 | 9/2014 | Aram et al. | |
| 2014/0275955 | A1 | 9/2014 | Crawford et al. | |
| 2014/0276853 | A1 | 9/2014 | Long et al. | |
| 2014/0277538 | A1* | 9/2014 | Sander | A61F 2/4202 623/20.32 |
| 2015/0320567 | A1 | 11/2015 | Terrill et al. | |
| 2016/0262903 | A1 | 9/2016 | West | |
| 2017/0100254 | A1* | 4/2017 | Lloyd | A61F 2/389 |
| 2018/0055648 | A1 | 3/2018 | Dhillon et al. | |
| 2018/0303490 | A1 | 10/2018 | Loring et al. | |
| 2019/0070012 | A1 | 3/2019 | Leemrijse et al. | |
| 2019/0209080 | A1 | 7/2019 | Gullotti et al. | |
| 2020/0008959 | A1 | 1/2020 | Oh et al. | |
| 2020/0015867 | A1 | 1/2020 | Luna et al. | |
| 2020/0038189 | A1* | 2/2020 | Williams | A61F 2/42 |
| 2020/0113712 | A1 | 4/2020 | Luna et al. | |
| 2020/0330238 | A1 | 10/2020 | Calamel et al. | |
| 2020/0337850 | A1 | 10/2020 | Reiley | |
| 2021/0378753 | A1 | 12/2021 | Christen et al. | |
| 2022/0280307 | A1* | 9/2022 | Haddad | A61F 2/4202 |
| 2022/0316504 | A1* | 10/2022 | Kubacki | A61F 2/30 |

FOREIGN PATENT DOCUMENTS

| | | | | |
|---|---|---|---|---|
| CN | 107997857 | A * | 5/2018 | A61F 2/389 |
| DE | 2306552 | | 8/1974 | |
| DE | 3516743 | | 11/1986 | |
| DE | 44 34 539 | | 4/1996 | |
| DE | 19501069 | | 7/1996 | |
| DE | 10123517 | C1 | 11/2002 | |
| DE | 20303498 | | 8/2003 | |
| DE | 202008017199 | | 3/2009 | |
| DE | 202008017200 | | 3/2009 | |
| EP | 0377901 | | 10/1989 | |
| EP | 0528080 | | 2/1993 | |
| EP | 0530804 | | 10/1993 | |
| EP | 0626156 | | 11/1994 | |
| EP | 0512529 | B1 | 7/1995 | |
| EP | 0704193 | | 4/1996 | |
| EP | 0852934 | A1 * | 7/1998 | A61F 2/3886 |
| EP | 0896825 | | 2/1999 | |
| EP | 0938869 | | 9/1999 | |
| EP | 0613380 | | 12/1999 | |
| EP | 0993807 | | 4/2000 | |
| EP | 1074229 | | 2/2001 | |
| EP | 1077253 | | 2/2001 | |
| EP | 1120087 | | 8/2001 | |
| EP | 1129675 | | 9/2001 | |
| EP | 1132061 | | 9/2001 | |
| EP | 0732091 | | 12/2001 | |
| EP | 0814731 | | 8/2002 | |
| EP | 1234552 | | 8/2002 | |
| EP | 1234555 | | 8/2002 | |
| EP | 0809987 | | 10/2002 | |
| EP | 0833620 | | 10/2002 | |
| EP | 2124832 | | 12/2009 | |
| EP | 3187152 | A1 * | 7/2017 | A61F 2/30728 |
| FR | 2819714 | | 7/2002 | |
| GB | 1451283 | | 9/1976 | |
| GB | 2291355 | | 1/1996 | |
| GB | 2338899 | A * | 1/2000 | A61F 2/76 |
| GB | 2348373 | | 10/2000 | |
| JP | 8-173465 | | 7/1996 | |
| JP | 9-206322 | | 8/1997 | |
| JP | 2000093435 | | 4/2000 | |
| JP | 2002-102236 | | 4/2002 | |
| JP | 2008-537689 | | 9/2008 | |
| JP | 2009515610 | | 4/2009 | |
| KR | 101954936 | B1 * | 3/2019 | A61F 2/4684 |
| WO | WO 87/02882 | | 5/1987 | |
| WO | WO 90/009769 | | 9/1990 | |
| WO | WO 93/004710 | | 3/1993 | |
| WO | WO 93/009819 | | 5/1993 | |
| WO | WO 93/025157 | | 12/1993 | |
| WO | WO 95/027450 | | 10/1995 | |
| WO | WO 95/028688 | | 10/1995 | |
| WO | WO 95/030390 | | 11/1995 | |
| WO | WO 95/032623 | | 12/1995 | |
| WO | WO 96/024302 | | 8/1996 | |
| WO | WO 97/025942 | | 7/1997 | |
| WO | WO 97/026847 | | 7/1997 | |
| WO | WO 97/027885 | | 8/1997 | |
| WO | WO 97/038676 | | 10/1997 | |
| WO | WO 98/012994 | | 4/1998 | |
| WO | WO 98/20816 | | 5/1998 | |
| WO | WO 98/030617 | | 7/1998 | |
| WO | WO 98/32384 | | 7/1998 | |
| WO | WO 99/002654 | | 1/1999 | |
| WO | WO 99/008598 | | 2/1999 | |
| WO | WO 99/008728 | | 2/1999 | |
| WO | WO 99/042061 | | 8/1999 | |
| WO | WO 99/047186 | | 9/1999 | |
| WO | WO 99/051719 | | 10/1999 | |
| WO | WO 99/056674 | | 11/1999 | |
| WO | WO-9966864 | A1 * | 12/1999 | A61F 2/389 |
| WO | WO 00/009179 | | 2/2000 | |
| WO | WO 00/015153 | | 3/2000 | |
| WO | WO 00/035346 | | 6/2000 | |
| WO | WO 00/048550 | | 8/2000 | |
| WO | WO 00/059411 | | 10/2000 | |
| WO | WO 00/074554 | | 12/2000 | |
| WO | WO 01/010356 | | 2/2001 | |
| WO | WO 01/017463 | | 3/2001 | |
| WO | WO 01/019254 | | 3/2001 | |
| WO | WO 01/035968 | | 5/2001 | |
| WO | WO 01/045764 | | 6/2001 | |
| WO | WO 01/068800 | | 9/2001 | |
| WO | WO 01/070142 | | 9/2001 | |
| WO | WO 01/091672 | | 12/2001 | |
| WO | WO 02/000270 | | 1/2002 | |
| WO | WO 02/000275 | | 1/2002 | |
| WO | WO 02/002158 | | 1/2002 | |
| WO | WO 02/022013 | | 3/2002 | |
| WO | WO 02/022014 | | 3/2002 | |
| WO | WO 02/023483 | | 3/2002 | |
| WO | WO 02/034310 | | 5/2002 | |
| WO | WO 02/036147 | | 5/2002 | |
| WO | WO 02/096268 | | 12/2002 | |
| WO | WO 03/007788 | | 1/2003 | |
| WO | WO 03/037192 | | 5/2003 | |
| WO | WO 03/047470 | | 6/2003 | |
| WO | WO 03/051210 | | 6/2003 | |
| WO | WO 03/055400 | | 7/2003 | |
| WO | WO 2003/065907 | | 8/2003 | |
| WO | WO 04/043305 | | 5/2004 | |
| WO | WO 04/049981 | | 6/2004 | |
| WO | WO 05/051239 | | 6/2005 | |
| WO | WO 05/051240 | | 6/2005 | |
| WO | WO-2005063151 | A1 * | 7/2005 | A61F 2/28 |

(56) References Cited

FOREIGN PATENT DOCUMENTS

| | | | | |
|---|---|---|---|---|
| WO | WO 06/060795 | | 6/2006 | |
| WO | WO 06/127283 | | 11/2006 | |
| WO | WO 07/041375 | | 4/2007 | |
| WO | WO 2007/061983 | | 5/2007 | |
| WO | WO 07/092841 | | 8/2007 | |
| WO | WO-2008098250 | A2 * | 8/2008 | ........... A61F 2/4637 |
| WO | WO 08/112996 | | 9/2008 | |
| WO | WO 08/157412 | | 12/2008 | |
| WO | WO 2009/001083 | | 12/2008 | |
| WO | WO 09/111639 | | 9/2009 | |
| WO | WO2009158522 | | 12/2009 | |
| WO | WO 2010/099142 | | 9/2010 | |
| WO | WO 2010/120346 | | 10/2010 | |
| WO | WO 2010/121147 | | 10/2010 | |
| WO | WO 2011/110374 | | 9/2011 | |
| WO | WO2012121726 | | 9/2012 | |
| WO | WO2019009891 | | 4/2019 | |
| WO | WO2020124047 | | 6/2020 | |
| WO | WO 2020124052 | | 6/2020 | |
| WO | WO 2020242542 | | 12/2020 | |
| WO | WO-2021097491 | A1 * | 5/2021 | ......... A61B 17/7291 |
| WO | WO 2022015877 | | 1/2022 | |
| WO | WO 2022094052 | | 5/2022 | |

OTHER PUBLICATIONS

Anonymous: “Angle bracket (fastener)—Wikipedia”, May 22, 2021, 1 page.
Anonymous: “Light Tube—Wikipedia”, Mar. 4, 2021, 11 pages.
Anonymous: Newtonian Telescope—Wikipedia, May 23, 2021, 6 pages.
Argenson, et al., “Is There a Place for Patellofemoral Arthroplasty?, ”Clinical Orthopaedics and Related Research No. 321, 1995, pp. 162-167.
Birnbaum, et al., “Computer-Assisted Orthopedic Surgery with Individual Templates and Comparison to Conventional Operation Method,” Spine, Feb. 2001, pp. 365-369, vol. 26, No. 4.
Chelule, et al., “Computer Aided Design of Personalized Jigs in Total Knee Replacement,” 3rd Annual Meeting of CAOS Int'l Proc, Jun. 18-21, 2003, pp. 58-59, Spain.
Dare, S., Bobyn, J., Drouin, G., Dussault, R., Gariepy, R., “Use of Computerized Tomography and Numerical Control Machining for the Fabrication of Custom Arthroplasty Prostheses.” Second World Congress on Biomaterials, 10th Annual Meeting of the Society for Biomaterials, p. 233, Washington, D.C., Apr. 27-May 1, 1984.
DePuy Synthes, “Flexible Reamers for Intramedullary Nails” Surgical Technique, 22 pages, 2017.
De Winter, et al., “The Richards Type II Patellofemoral Arthroplasty,” Acta Orthop Scand, 2001, pp. 487-490, 72(5).
Delp, et al., “A Graphics-Based Software System to Develop and Analyze Models of Musculoskeletal Structures,” Comput. Biol. Med., 1995, pp. 21-34, vol. 25, No. 1.
Farrar, et al., “Computed Tomography Scan Scout Film for Measurement of Femoral Axis in Knee Arthroplasty,” J. Arthroplasty, 1999, pp. 1030-1031, vol. 14, No. 8.
Final Official Action for U.S. Appl. No. 13/465,547, dated Feb. 26, 2014.
First Office Action for Japanese Patent Appln. No. 2011-552091, dated Oct. 25, 2013.
Froemel, et al., “Computer Assisted Template Based Navigation for Total Knee Replacement,” Documents presented at CAOS on Jun. 17, 2001, 4 pages.
Hafez, et al., “Computer Assisted Total Knee Replacement: Could a Two-Piece Custom Template Replace the Complex Conventional Instrumentations?”, 4th Annual Meeting of CAOS Int'l Proc, Jun. 16-19, 2004, pp. 63-64, Chicago.
Hafez, et al., “Computer-Assisted Total Hip Arthroplasty: The Present and the Future,” Future Rheumatol., 2006, pp. 121-131, vol. 1.
Kim, et al., “Measurement of Femoral Neck Anteversion in 3D. Part 1: 3D Imaging Method,” Med. and Biol. Eng. and Computing, 2000, pp. 603-609, vol. 38, No. 6.
Lam, et al., “X-Ray Diagnosis: A Physician's Approach,” 1998, Title page and Table of Contents pages Only, ISBN 9813083247, Springer-Verlag publishers.
Lam. et al . . . “VarusNalgus Alignment of the Femoral Component in Total Knee Arthroplasty,” The Knee, 2003, pp. 237-241, vol. 10.
Lu, et al., “In Vitro Degradation of Porous poly(L-lactic acid) Foams,” Biomaterials, Aug. 2000, pp. 1595-1605, 21(15).
Mahaisavariya, et al., “Morphological Study of the Proximal Femur: a New Method of Geometrical Assessment Using 3-Dimensional Reverse Engineering”, Medical Engineering & Physics 24 (2002) pp. 617-622.
Marler, et al., “Soft-Tissue Augmentation with Injectable Alginate and Synegeneic Fibroblasts,” Plastic & Reconstructive Surgery, May 2000 pp. 2049-2058, 105(6).
PCT/US2010/025143, International Preliminary Report on Patentability and Written Opinion, Sep. 9, 2011.
Portheine, et al., “Potentials of CT-based Planning and Template-based Procedure in Hip and Knee Surgery,” Orth. Prac, 2000, pp. 786-791, vol. 36, English Translation with Certification.
Radermacher, “Computer Assisted Matching of Planning and Execution in Orthopedic Surgery,” Slide Presentation, Nov. 29, 1993, 22 pages.
Radermacher, “Template Based Navigation—An Efficient Technique for Hip and Knee Surgery,” CAOS First Asian Meet, Mar. 27-28, 2004, pp. 45-50, India.
Radermacher, et al., “Computer-Assisted Planning and Operation in Orthopedics,” Orth. Prac 36th Year, Dec 2000, pp. 731-737, English Translation with Certification.
Rau, et al., “Small and Neat,” Medical Tech. Int'l, 1993-94, pp. 65, 67 and 69.
Schkommadau, et al., “Clinical Experience With the Individual Template Technique,” Orth. Prac, 2001, pp. 19-22, vol. 37, No. 1, English Translation with Certification.
Seel, et al., “Three-Dimensional Planning and Virtual Radiographs in Revision Total Hip Arthroplasty for Instability,” Clinical Orthopaedics and Related Research, Jan. 2006, pp. 35-38, No. 442.
Slone, et al., “Body CT: A Practical Approach,” 1999, Title page and Table of Contents pages Only, ISBN 007058219, McGraw-Hill.
Staudte, et al., “Computer-Assisted Operation Planning and Technique in Orthopedics,” North Rhine-Westphalia Acad. for Sciences, Lecture N.444, 2000, 17 pages, ISSN 0944-8799, in German.
Staudte, et al., “Computer-Assisted Operation Planning and Technique in Orthopedics,” North Rhine-Westphalia Acad. for Sciences, Lecture N.444, 2000, 34 pages, ISSN 0944-8799, English Translation with Certification.
Stauffer, et al., “The Macintosh Prosthesis. Prospective Clinical and Gait Evaluation,” Arch. Surg., 1975, pp. 717-720, 110(6).
Stout, et al., “X-RAY Structure Determination: A Practical Guide,” 1989, Title page and Table of Contents pages Only, ISBN 0471607118, John Wiley & Sons.
Stryker Trauma GmbH, “Bixcut Reamer System” Osteosynthesis, 8 sheets, 2009.
Synthes, “SynReam, The Synthes Reaming System” Surgical Technique, 22 pages, 2005.
Tamez-Pena, et al., “MRIlsotropic Resolution Reconstruction from Two Orthogonal Scans,” Proceedings of the SPIE—The International Society for Optical Engineering SOIE-OMT, 2001, pp. 87-97, vol. 4322.
Testi, et al., “Border Tracing Algorithm Implementation for the Femoral Geometry Reconstruction,” Camp. Meth. and Programs in Biomed., 2001, pp. 175-182, vol. 65.
Vandeberg, et al., “Assessment of Knee Cartilage in Cadavers with Dual-Detector Spiral CT Arthrography and MR Imaging,” Radiology, Feb. 2002, pp. 430-435, 222(2).
Wiese, et al., “Biomaterial Properties and Biocompatibility in Cell Culture of a Novel Self-Inflating Hydrogel Tissue Expander,” J. Biomedical Materials Research Part A, Nov. 2000, pp. 179-188, 54(2).

(56) References Cited

OTHER PUBLICATIONS

Woolson, S., Fellingham, L., Dev, P., and Vassiliadis, A., "Three Dimensional Imaging of Bone from Analysis of Computed Tomography Data." Orthopedics, vol. 8, No. 10, pp. 1269-1273, Oct. 1985.
Yusof, et al., "Preparation and Characterization of Chitin Beads as a Wound Dressing Precursor," J. Biomedical Materials Research Part A, Oct. 2000, pp. 59-68, 54(1).
Examination Report issued in connection with corresponding Indian Patent Application No. 2004/KOLNP/2013, Nov. 27, 2018, 7 pages.
First Office Action issued in connection with corresponding Chinese Patent Application No. 201610973637.8, Nov. 28, 2018, 6 pages.
First Examination Repot issued in connection with corresponding Australian Patent Application No. 2018204063, Jul. 10, 2019, 2 pages.
Second Examination Report issued in connection with corresponding Australian Patent Application No. 2019261830, May 4, 2021, 9 pages.
First Examination Repot issued in connection with corresponding Australian Patent Application No. 201926183, Dec. 21, 2020, 4 pages.
International Search Report and Written Opinion issued in connection with International Patent Application No. PCT/US2022/070130, May 13, 2022, 17 pages.
Extended European Search Report issued in connection with European Application No. 22172072, May 4, 2023, 25 pages.
Extended European Search Report issued in connection with corresponding European Patent Application No. 23185897.8, Feb. 1, 2024, 11 pages.

* cited by examiner

COUPLING SYSTEMS AND METHODS

CROSS-REFERENCE TO RELATED APPLICATION

This application claims priority under 35 U.S.C. § 119(e) to U.S. Provisional Application No. 63/378,714, filed Oct. 7, 2022, the entirety of which is incorporated herein by reference.

INCORPORATION BY REFERENCE

This application is related to commonly owned U.S. patent application Ser. No. 12/410,978 filed on Mar. 25, 2009, now U.S. Pat. No. 8,715,362, U.S. patent application Ser. No. 16/605,849, which is a U.S. national phase entry under 35 U.S.C. § 371 of international patent application No. PCT/US2017/040730 filed on Jul. 5, 2017, U.S. patent application Ser. No. 17/650,116 filed on Feb. 7, 2022 and U.S. Provisional Application No. 63/269,269 filed on Mar. 14, 2022 the entireties of which are incorporated by reference herein.

FIELD OF DISCLOSURE

The disclosed systems and methods relate to implants. More particularly, the disclosed systems and methods relate to the coupling and decoupling of two or more stemmed components of a prosthesis or implant.

BACKGROUND

Medical prostheses are available to address any number of abnormalities. For example, a prosthesis may be provided to replace a joint, such as a shoulder, elbow, knee, or ankle. Each prosthesis may include one or more components, such as a stem that is to be inserted into a passageway formed along an axis of a bone, and a tray that is to be coupled to the stem. A tray may support one or more additional components, such as an articular surface formed from metal or polymer that may be coupled to the tray. In order to speed recovery and reduce complications, surgical techniques seek to minimize the size or length of an incision or access site needed to install a prosthesis and maximize the efficiency of the operation. As a result, there continues to be a need to minimize the size of the implant to be installed and improve the efficiency of the operation.

SUMMARY

In some embodiments, a system may include a first component, an engagement element, a biasing member, and a securing mechanism. The first component may have a first body extending from a first face to a second face. The engagement element may be disposed on the first face of the first body and may be configured to engage a second component. The biasing member may be disposed on the engagement element and may be configured to latch a second component to the first component. The securing mechanism may be configured to receive a locking mechanism at an angle with respect to a longitudinal axis. The locking mechanism may be adapted to interact with the biasing member.

In some embodiments, a method may include coupling a first component to a second component by aligning a pair of rails on the first component to a pair of rails on the second component sliding the second component in a posterior direction to engage the pair of rails of the second component with the pair of rails on the first component.

In some embodiments, a method may include decoupling a first component from a second component. The first and second components may both include a respective body. The respective bodies may include respective spaced apart rails of the first and second component. The decoupling may include unlocking the first and second components by uninstalling a locking mechanism from a securing mechanism disposed, at an angle with respect to a longitudinal axis of the first component on an outer surface of the first component. The removal of the locking mechanism may move a biasing member into a second position. The decoupling may include moving the first and second components apart by sliding the respective spaced apart rails away from each other by pulling an extraction tool handle in a posterior direction.

In some embodiments, a system may include a first component, a pair of rails, and a biasing member. The first component may include a first body extending from a first face to a second face. The pair of rails may be disposed on the first face of the first body. The pair of rails may be configured to engage a second component. The biasing member may be disposed on the first face of the first body and may be configured to latch the first and second component together.

In some embodiments, a method may include coupling a first component and a second component together by aligning a respective pair of rails of the first and second components and locking the first and second components together with an engagement element disposed on a first face of the second component. The engagement element may include a tab, a cut out, an angled slope, and a ledge. The tab may be configured to fit inside of a detent. The cut out on the bottom side of the tab may be configured to allow the tab to bend. The angled slope may be adapted to allow a removal tool access. The ledge may be on the first end of the tab. The ledge may be adapted to lock inside of a detent on a bottom end of the first component.

In some embodiments, a method may include decoupling a first component from a second component. The first and second components may include a respective body. The respective bodies may include respective spaced apart rails. The decoupling may include sliding a removal tool along an angled slope on the body of the second component. The removal tool may be adapted to engage a tab on the second component and may remove the tab from a detent on a second face of the first component. If the tab is removed from the detent, moving the respective spaced apart rails of the first and second component apart by pulling an extraction tool handle in a posterior direction completing the decoupling.

DETAILED DESCRIPTION

Figure 1:
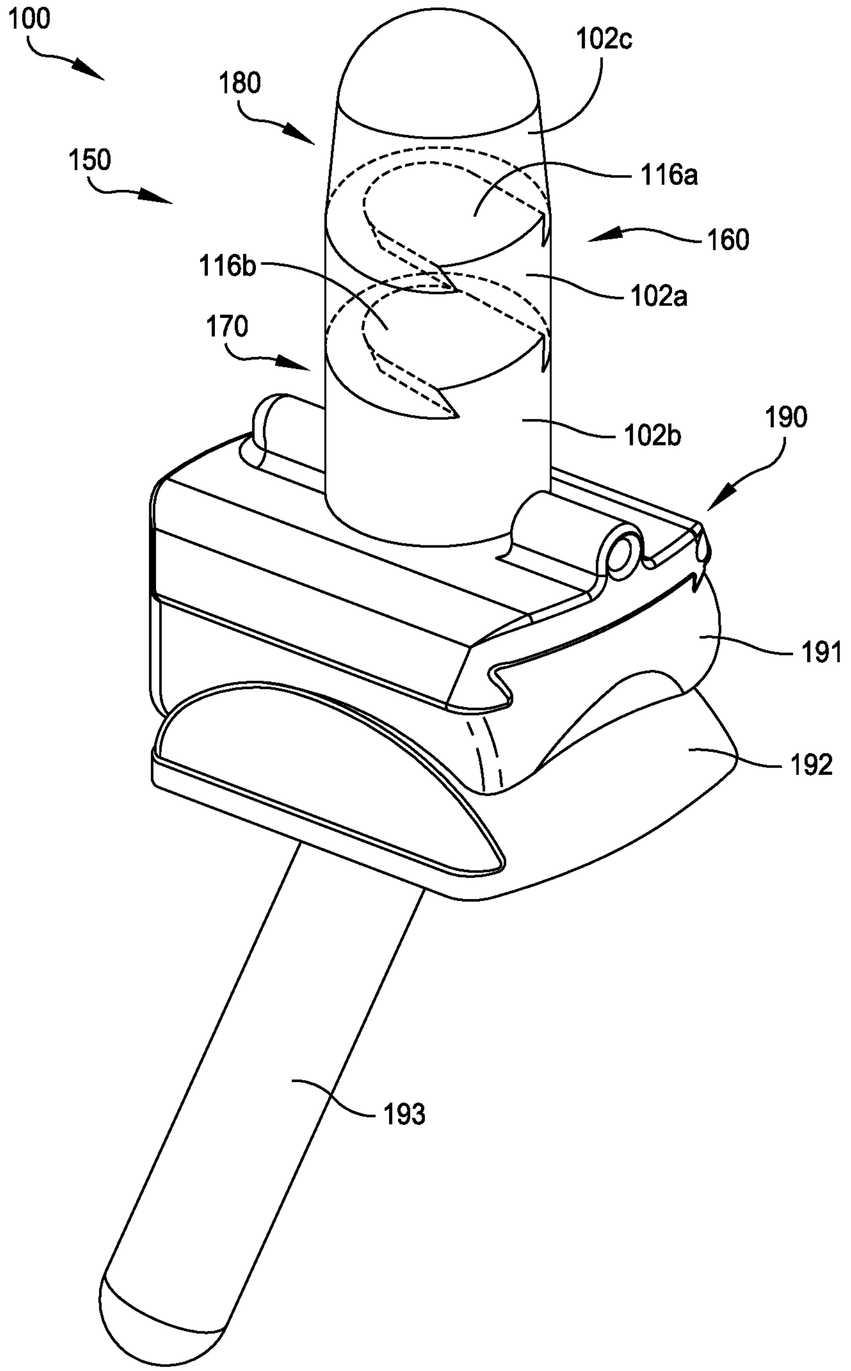
FIG. 1 is an isometric view of an example of a prosthesis system having a coupling mechanism in accordance with some embodiments.

This description of the exemplary embodiments is intended to be read in connection with the accompanying drawings, which are to be considered part of the entire written description.

The disclosed components, systems, and methods provide for coupling together two or more components of a medical prosthesis and facilitate the coupling together of the various components. The disclosed components, systems, and methods also provide for decoupling two or more components of a medical prosthesis to facilitate removal of the components. In some embodiments, the components may be coupled together in situ through a minimally invasive opening, although it should be understood that the components may be coupled together ex situ and implanted as a single construct. In some embodiments, two or more components may be assembled ex situ to form a first assembly, and at least one third component may be assembled to the first assembly in situ to form a second assembly. One or more fourth components may be assembled to the second assembly in situ. Although the following descriptions are provided with reference to an ankle prosthesis, such as the INBONE™ Total Ankle System available from the Wright Medical Group and the ankle prostheses disclosed in U.S. Pat. No. 8,715,362, entitled "Ankle Replacement System," which is incorporated by reference herein in its entirety, it should be understood that the disclosed systems and methods are not to be limited to such prosthesis and may be used in connection with any number of different prosthesis, including prostheses for joints other than ankles. For example, the disclosed components, systems, and methods may be applied to prosthesis for other joints including, but not limited, hips, shoulders, elbows, and knees, to list only a few possibilities.

FIGS. 1-9 illustrate one example of a system 100 including a coupling mechanism in accordance with some embodiments. In some embodiments, the system 100 may be an ankle prosthesis including a stem 150, a tibia tray component 190, a tibial artificial joint surface 191, a talar component 192 with artificial surface, and a talar stem 193. The stem 150 may be a multi-component stem including two or more components that may be coupled by a coupling mechanism, which may be a dovetail coupling mechanism, as described herein. Although the components described herein are described with reference to an ankle prosthesis, the components, systems, and methods are not so limited, as one of ordinary skill in the art will understand that the components may be adapted for other prosthesis, including the hip, knee, and shoulder, to list only a few possible examples.

Figure 2:
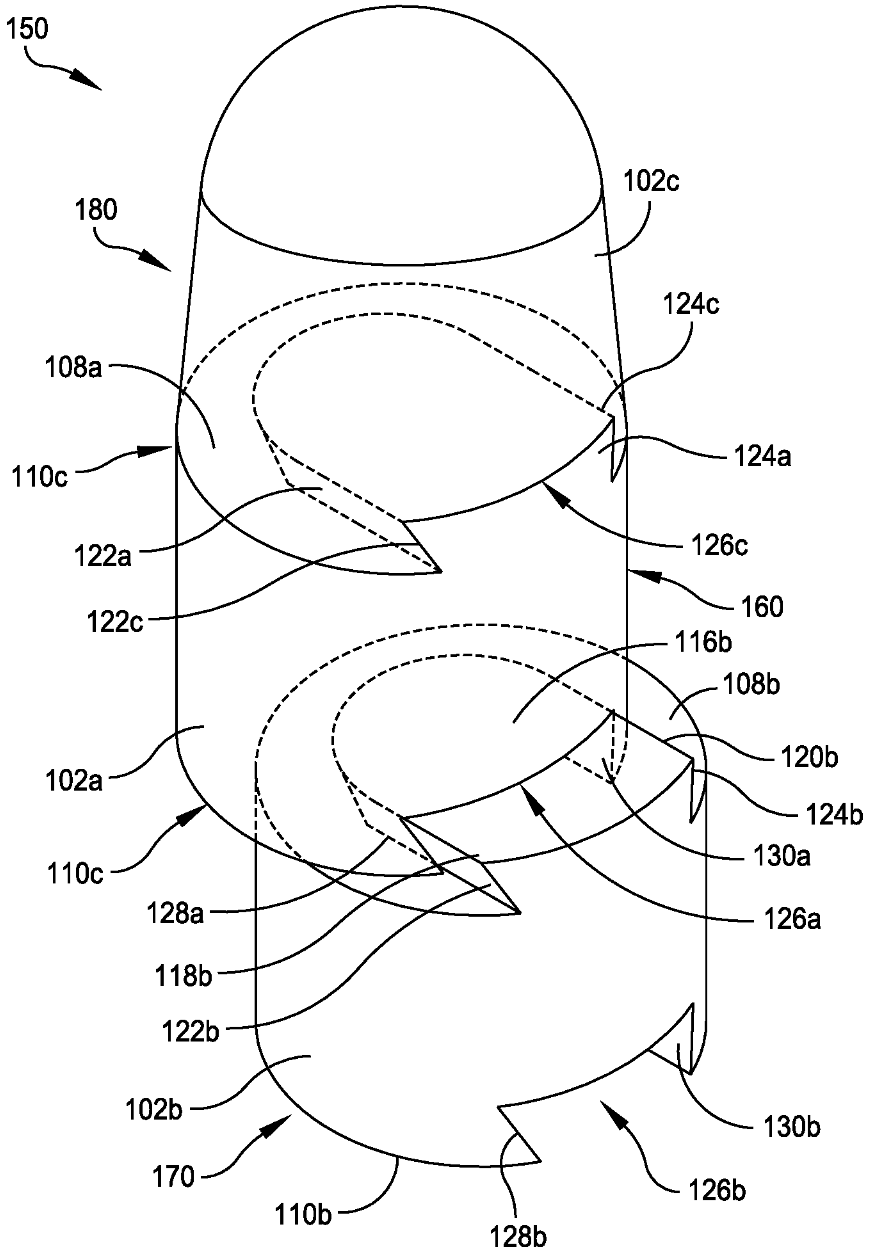
FIG. 2 is an isometric view of the stem components of the system illustrated in FIG. 1 in accordance with some embodiments.
Figure 3:
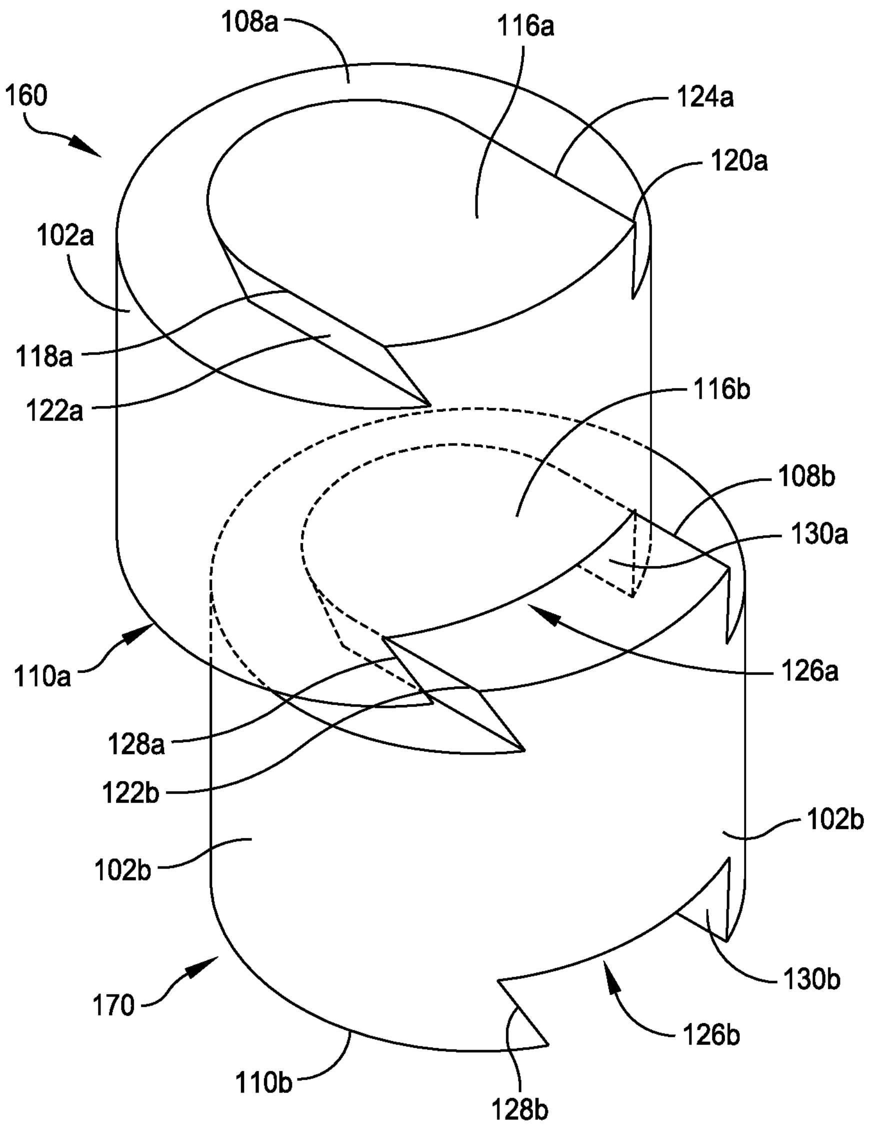
FIG. 3 is an isometric view of stem components of the system illustrated in FIG. 1 in accordance with some embodiments.
Figure 4:
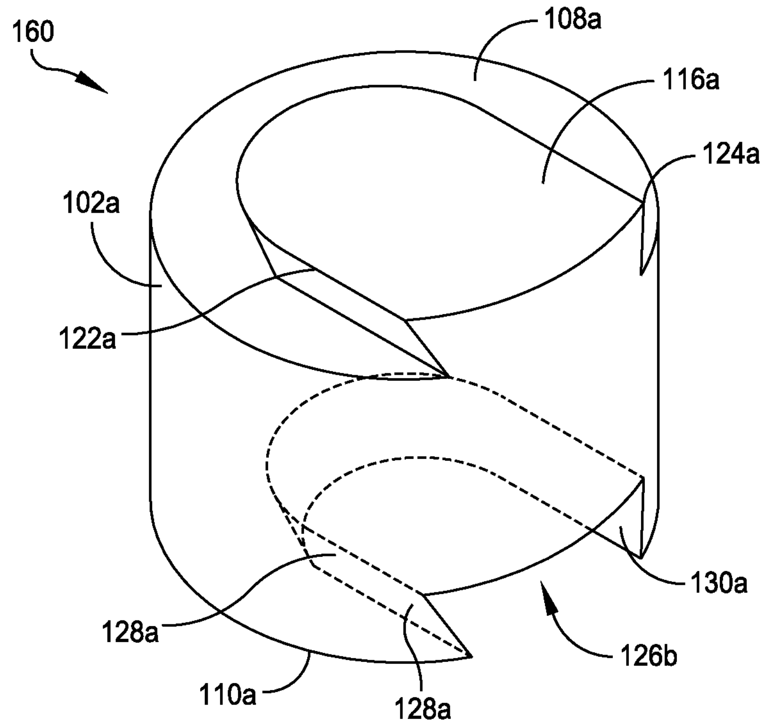
FIG. 4 is an isometric view of the middle stem component of the system illustrated in FIG. 1 in accordance with some embodiments.
Figure 5:
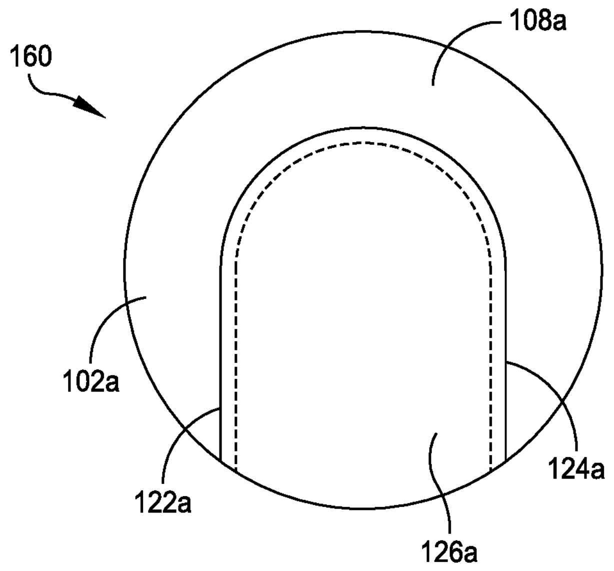
FIG. 5 is a top side perspective view of the middle stem component of the system illustrated in FIG. 1 in accordance with some embodiments.
Figure 6:
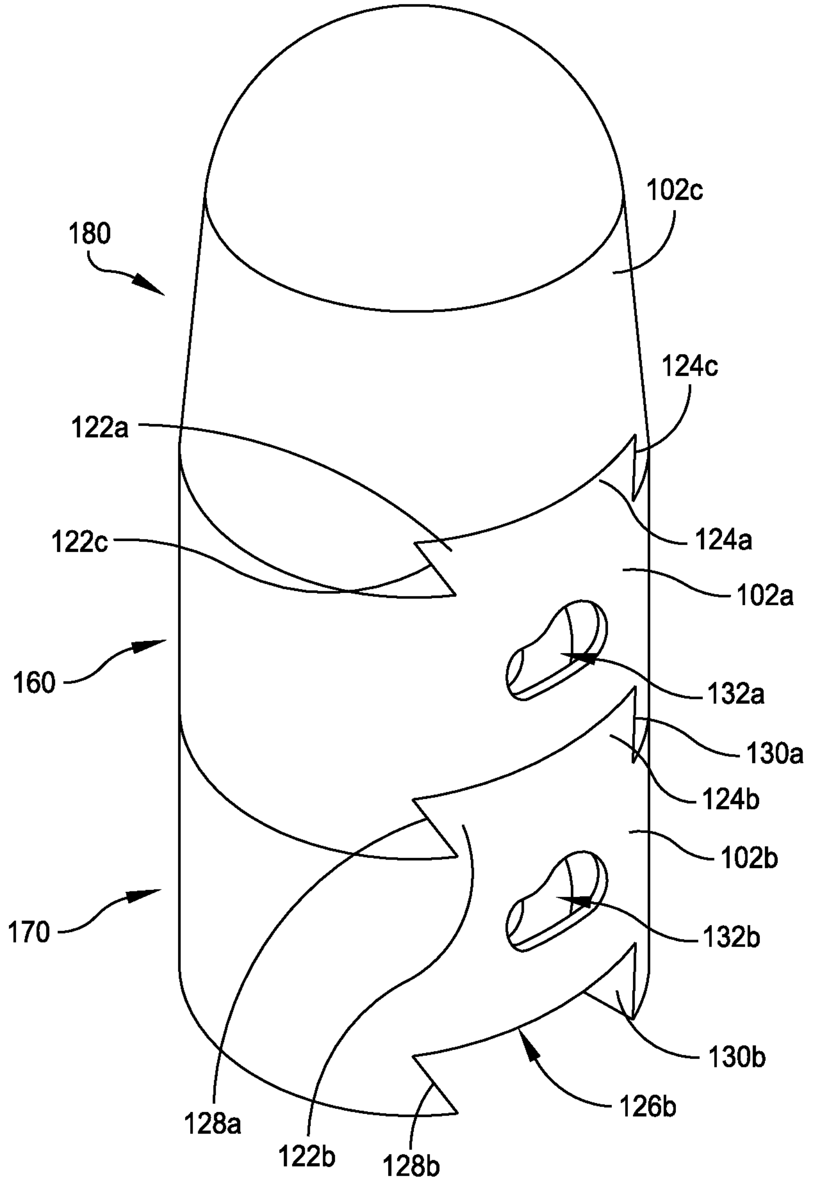
FIG. 6 is an isometric view of stem components of the system illustrated in FIG. 1 configured to allow removal with an extraction tool in accordance with some embodiments.
Figure 7:
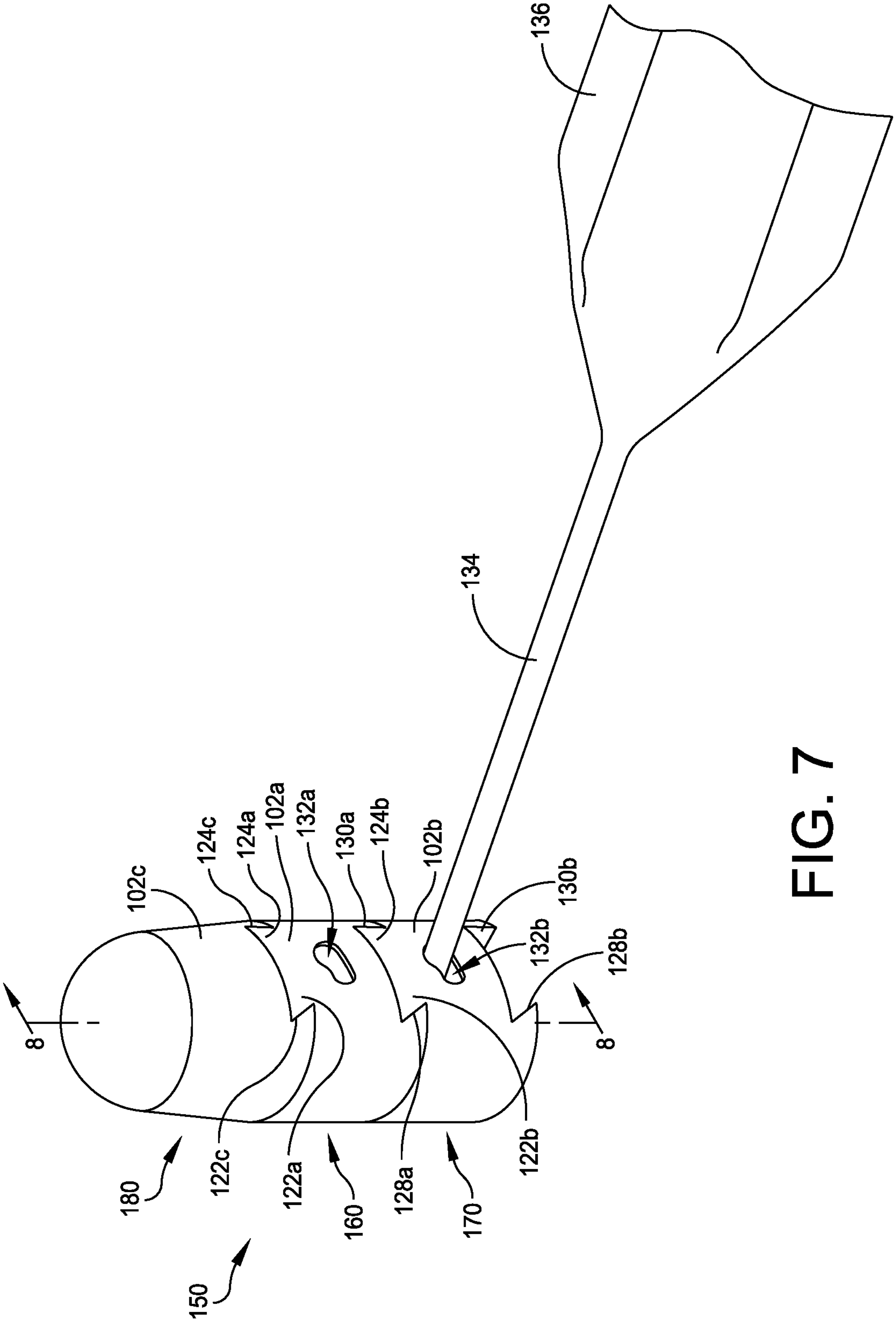
FIG. 7 is an isometric view of stem components of the system illustrated in FIG. 6 including an extraction tool in accordance with some embodiments.
Figure 8:
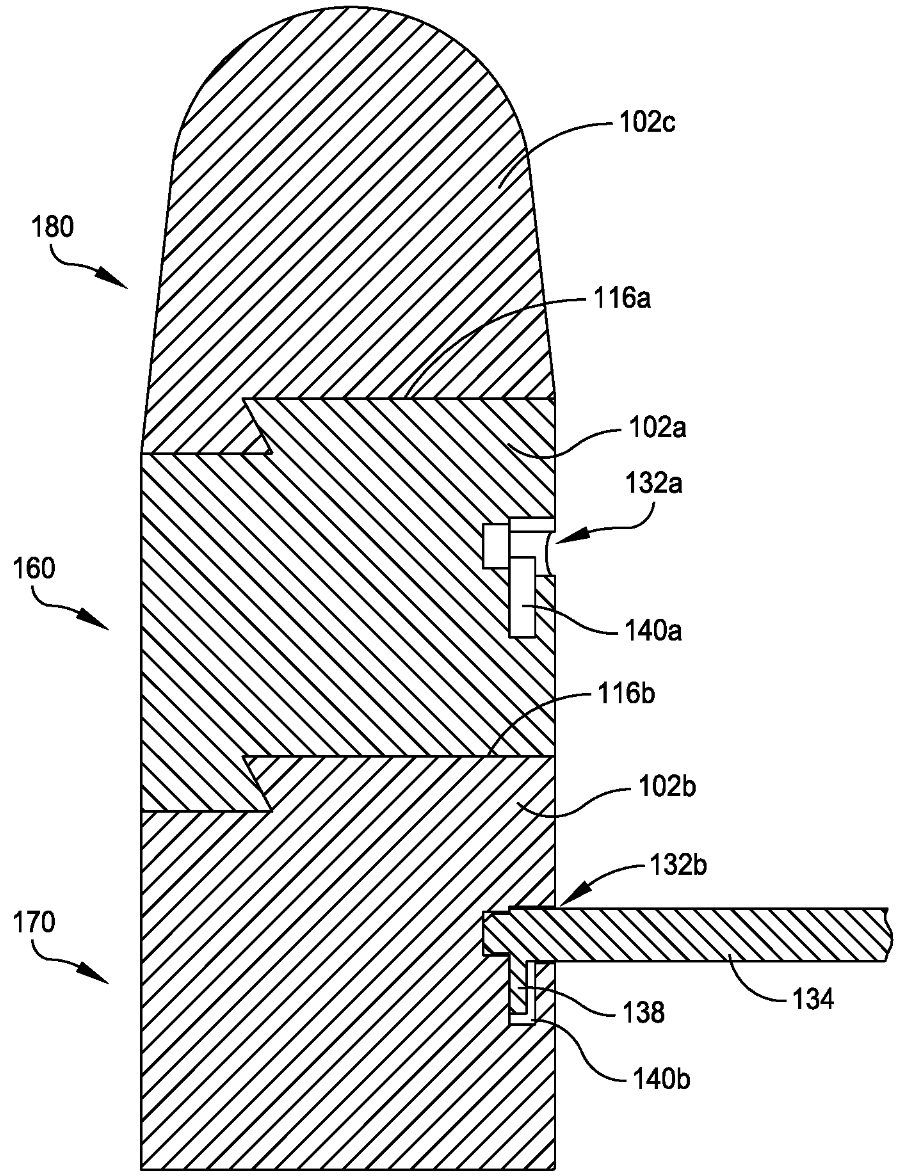
FIG. 8 is a cross-sectional view of stem components illustrated in FIG. 7, in a first position, taken along line 8-8 in FIG. 7 in accordance with some embodiments.
Figure 9:
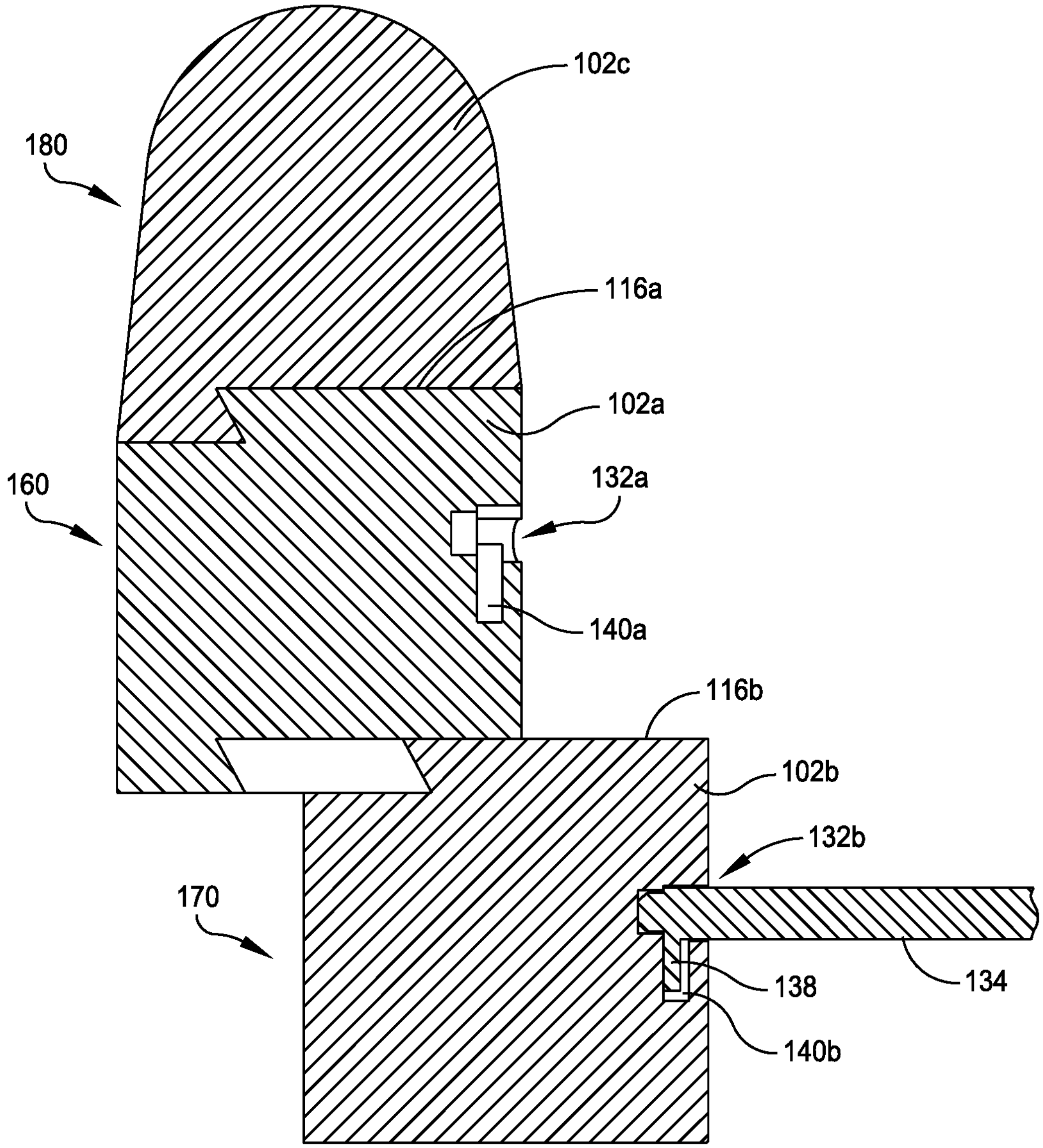
FIG. 9 is a cross-sectional view of stem components illustrated in FIG. 7, in a second position, taken along line 8-8 in FIG. 7 in accordance with some embodiments.

In the example illustrated in FIG. 2, the stem 150 includes a first component 180, which may be a top or leading component, a second component 160, which may be a middle component, and a third component 170, which may be a bottom component or another middle component. It should be understood that the second and third components may be identical or different depending on the length and configuration of the stem, as described herein. In some embodiments, the components 160, 170, 180 may be coupled together either in situ or ex situ.

Each of the stem components 160, 170, 180 may include a body 102*a*, 102*b*, 102*c* having a generally cylindrical shape, with stem component 180 tapering along its length from a first diameter at leading end to a second diameter at its trailing end. In some embodiments, the second diameter is greater than the first diameter. It should be understood that stem components 160, 170, 180 may have other shapes or configurations (e.g., conical, pyramidal, cubic, and/or oval, to list only a few examples). In addition, the stem components 160, 170, 180 could be arched to reduce and/or prevent rotation, and could be of constant or varying cross-sectional widths. In some embodiments, the stem components 160, 170, 180 may include one or more anti-rotation features extending radially outward from the body 102*a*, 102*b*, 102*c*, as will be understood by one of ordinary skill in the art. Examples of such anti-rotation features are described in U.S. Patent Application Publication No. 2022/0280307 and U.S. Provisional Application No. 63/374,248, filed Sep. 1, 2022, which are incorporated by reference herein in its entirety. Body 102*a*, 102*b*, 102*c* may be formed using an additive manufacturing process, such as Direct Metal Laser Sintering (DMLS) or Electron Beam Melting (EBM), to list only a few possibilities. Other conventional manufacturing processes, such as machining, molding, extruding, and combinations thereof, may also be used as will be understood by one of ordinary skill in the art.

In some embodiments, body 102*c* of leading component 180 further include a second face 110*c*. The second face 110*c* may define a pair of spaced apart rails 122*c* and 124*c*, disposed within channel 126*c*, configured to slide along spaced apart rails of another prosthesis component (e.g., stem component 160, 170 and/or another stem component of a multi-component stem) to form a dovetail coupling.

In some embodiments, the body 102*a* of stem component 160 may further include a first face 108*a* and a second face 110*a*. The first face 108*a* may, in some embodiments, define an engagement element 116*a*, such as a shelf or one or more flats, having a first edge 118*a* and a second edge 120*a*. The first 118*a* and second 120*a* edges includes spaced apart rails, 122*a* and 124*a* respectively, configured to slide along spaced apart rails within a channel disposed on the second face of another prosthesis component (e.g., prosthesis component 160, 170 and/or another stem component, such as leading component 180, of a multi-component stem) to form a dovetail coupling. The second face 110*a*, in some embodiments, further includes a pair of spaced apart rails 128*a* and 130*a*, disposed within channel 126*a*, configured to slide along spaced apart rails of another prosthesis component (e.g., stem component 160, 170 and/or another stem component of a multi-component stem) to form a dovetail coupling. One of ordinary skill in the art will understand that other engagement elements may be used instead of flats, rails, or shelfs.

In some embodiments, the body 102*b* of stem component 170 may further include a first face 108*b* and a second face 110*b*. The first face 108*b* may, in some embodiments, define an engagement element 116*b*, such as a shelf or one or more flats, having a first edge 118*b* and a second edge 120*b*. The first 118*b* and second 120*b* edges includes spaced apart rails, 122*b* and 124*b* respectively, configured to slide along spaced apart rails within a channel disposed on the second face of another prosthesis component (e.g., prosthesis component 160, 170 and/or another stem component, such as leading component 180, of a multi-component stem) to form a dovetail coupling. The second face 110*b*, in some embodiments, further includes a pair of spaced apart rails 128*b* and 130*b*, disposed within channel 126*b*, configured to slide along spaced apart rails of another prosthesis component (e.g., stem component 160, 170 and/or another stem component of a multi-component stem) to form a dovetail coupling. One of ordinary skill in the art will understand that other engagement elements may be used instead of flats, rails, or shelfs.

In some embodiments, a leading component 180, may be attached to components 160 and/or 170. For example, the body 102*c* of component 180 may be inserted into a resected joint space between first and second bones, which may be a tibia and a talus. The component 180 may be advanced, at least partially, into an intramedullary canal form in one of the bones (e.g., the tibia). Component 160 may then be coupled to the component 180 by aligning spaced apart rails 122*a*, 124*a* and 122*c*, and 124*c* of the two components 160, 180. Once aligned, component 160 may be pushed into engagement (e.g., by pushing in a first direction such as backward or in a posterior direction) so that engagement element 116*a* on the first face 108*a* of component 160 contacts the back end of the channel 126*c*. In some embodiments, a locking mechanism, such as a set screw, may be placed in an opening penetrating a side of the body 102*c* and into engagement element 116*a* locking the two components 160, 180 together. Stem component 160 may be installed by hand and/or by using a tool fitted around the body to install the two components 160, 180 together. One of ordinary skill in the art will understand that other engagement elements may be used, such as a spring-loaded detent or a depression and projections.

Bottom or middle component 170 may be coupled to middle component 160 by aligning the spaced apart rails 128*a*, 130*a* and 122*b*, 124*b* of the two components 160,170. Once aligned, component 170 may be pushed into engagement (e.g., by pushing in a first direction such as backward or in a posterior direction) so that engagement element 116*b* on the first face of component 170 contacts the back end of the channel 126*a*. In some embodiments, a locking mechanism, such as a set screw, may be placed in an opening penetrating a side of the body 102*a* and into the engagement element 116*b* locking the two components 160, 170 together. Stem component 160 may be installed by hand and/or by using a tool fitted around the body to install the two components 160, 170 together. One of ordinary skill in the art will understand that other engagement elements may be used, such as a spring-loaded detent or a depression and projections.

Figure 17:
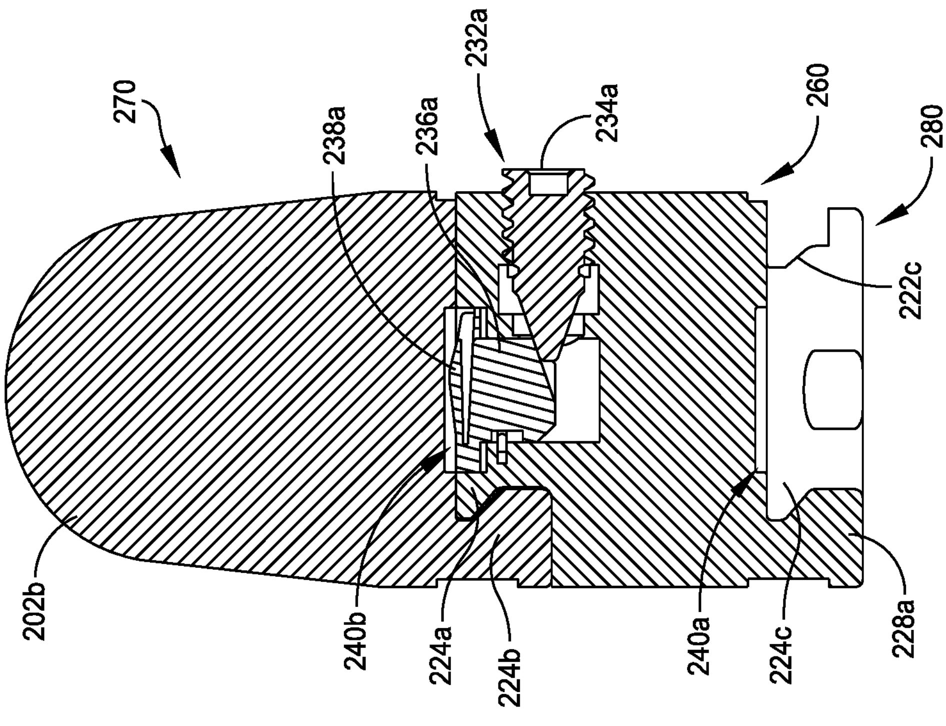
FIG. 17 is a cross-sectional view of the stem components illustrated in FIG. 13, in a third position, taken along line 15-15 in FIG. 13 in accordance with some embodiments.
Figure 18:
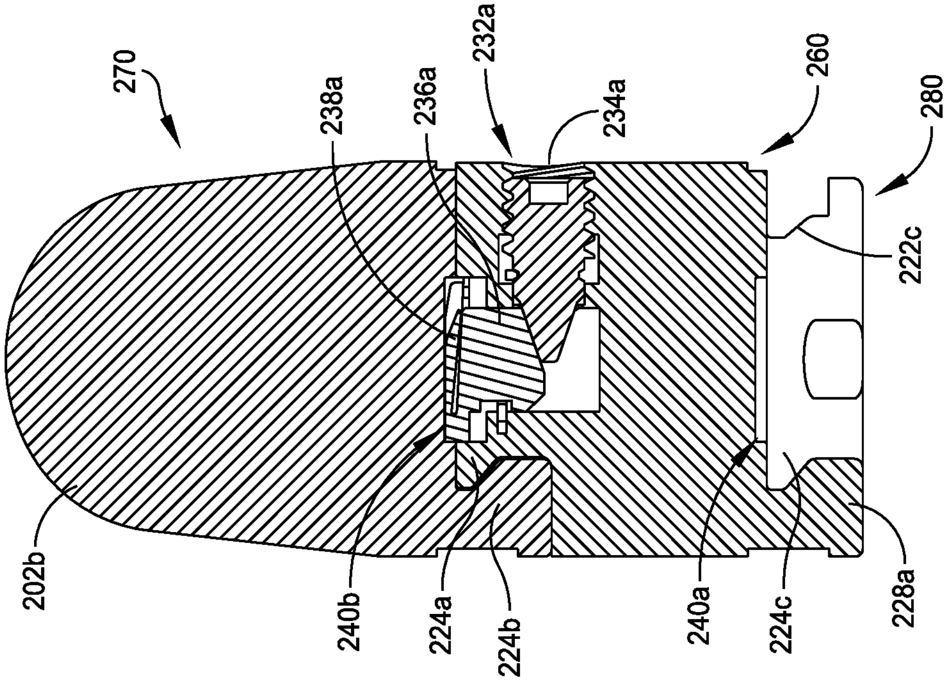
FIG. 18 is a cross-sectional view of the stem components illustrated in FIG. 13, in a fourth position, taken along line 15-15 in FIG. 13 in accordance with some embodiments.
Figure 19:
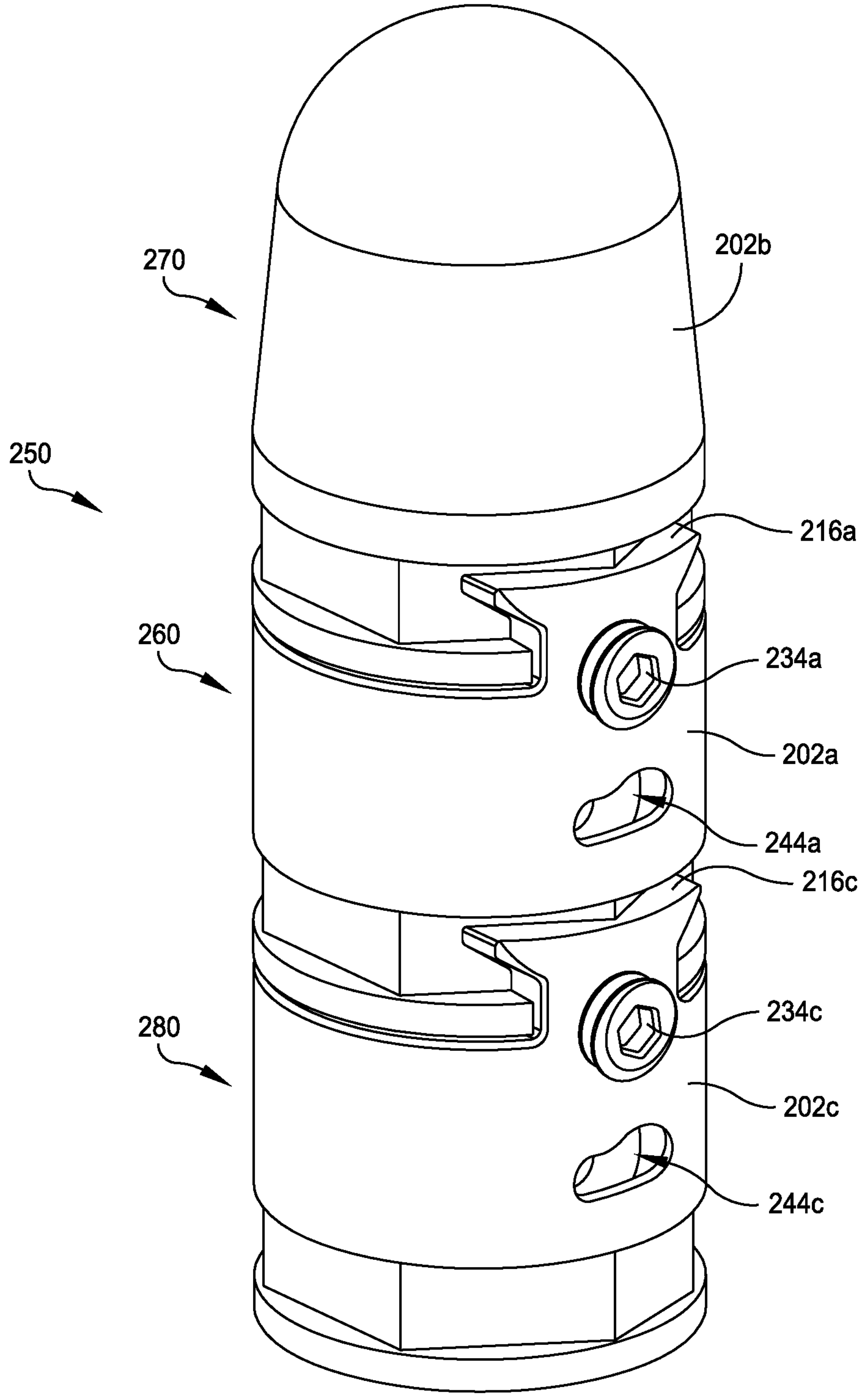
FIG. 19 is an isometric view of stem components of the system illustrated in FIG. 10 configured to allow removal with an extraction tool in accordance with some embodiments.
Figure 20:
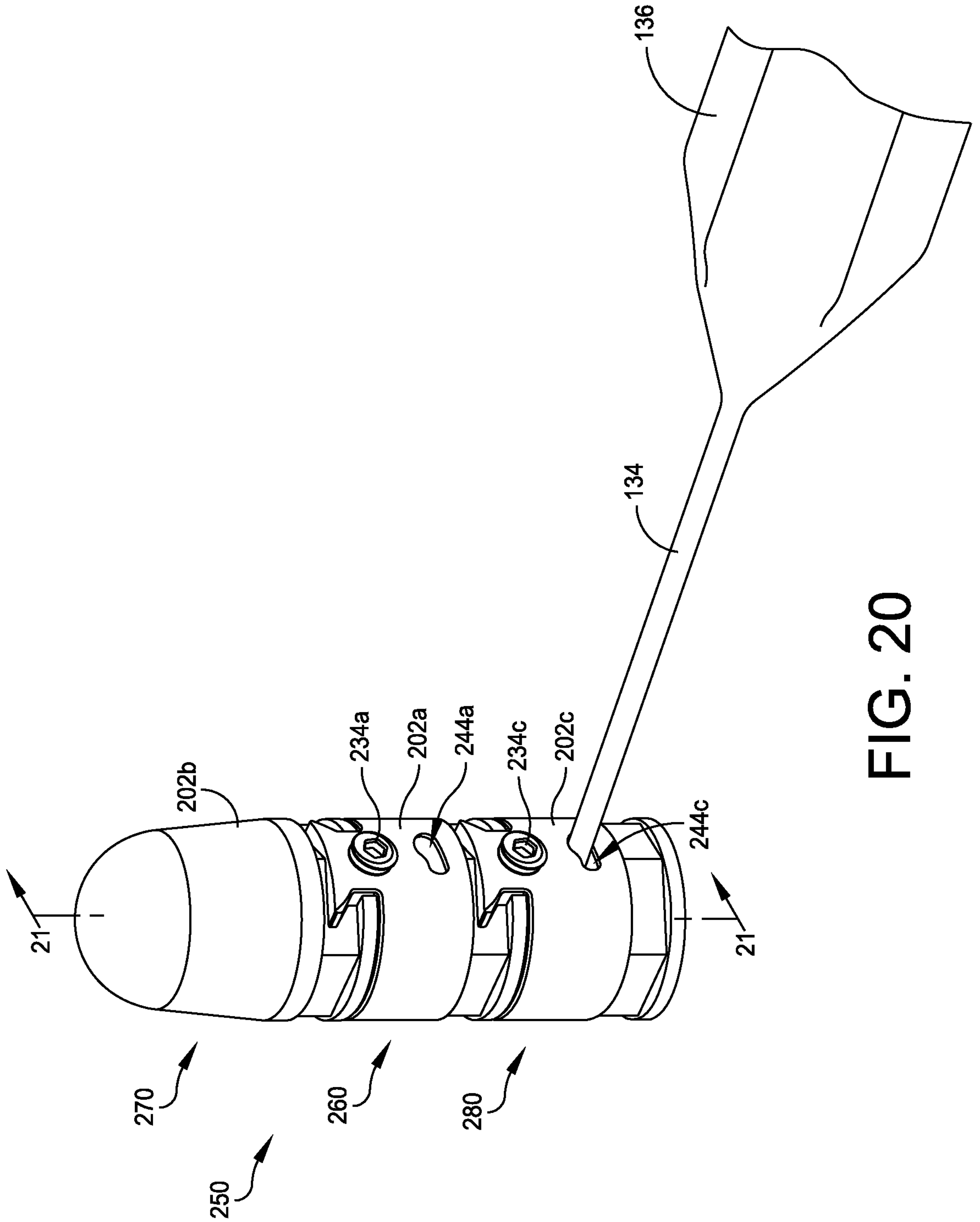
FIG. 20 is an isometric view of stem components of the system illustrated in FIG. 19 including an extraction tool in accordance with some embodiments.
Figure 21:
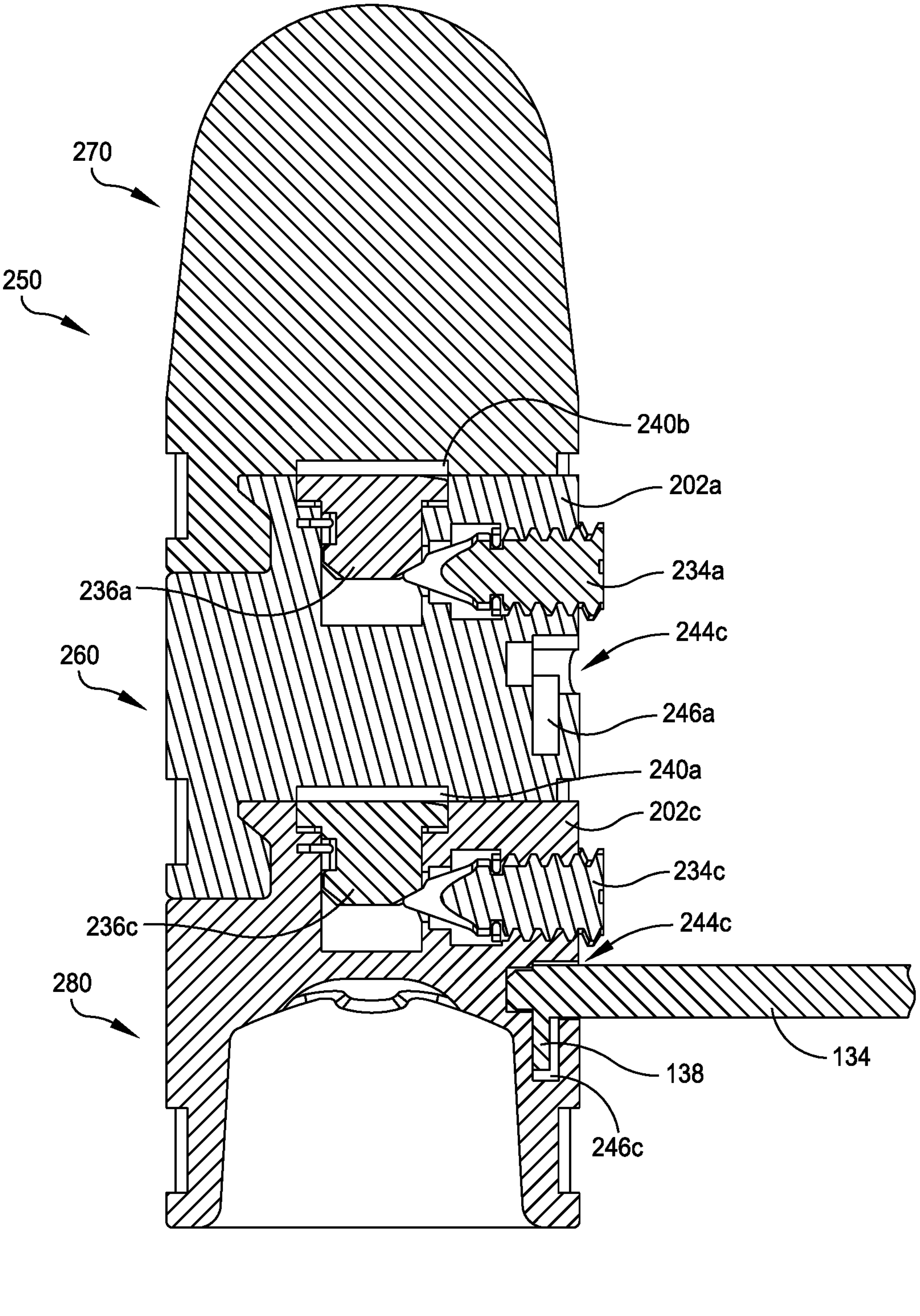
FIG. 21 is a cross-sectional view of stem components illustrated in FIG. 20, in a first position, taken along line 21-21 in FIG. 20 in accordance with some embodiments.
Figure 22:
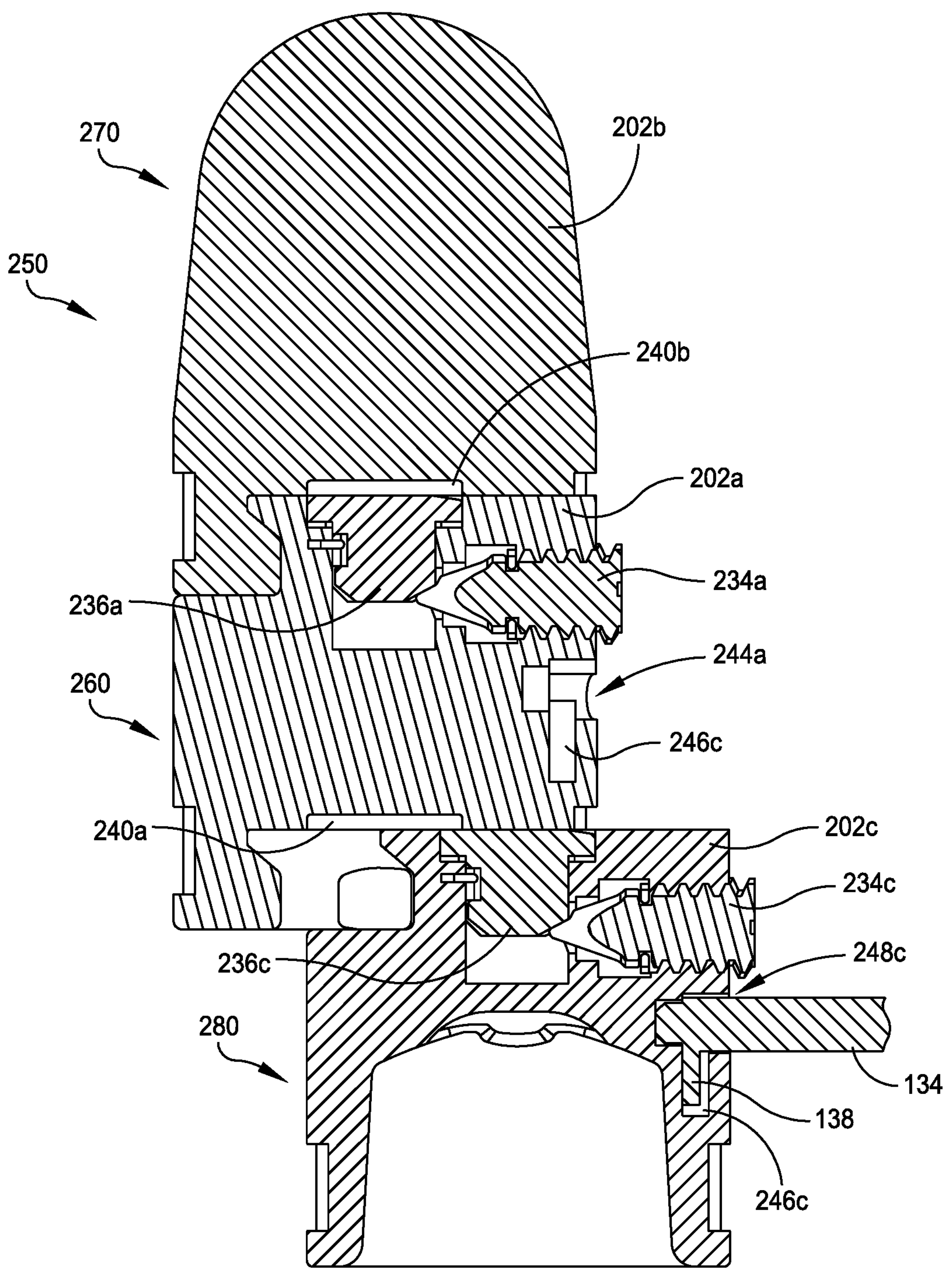
FIG. 22 is a cross-sectional view of stem components illustrated in FIG. 20, in a second position, taken along line 21-21 in FIG. 20 in accordance with some embodiments.

In some embodiments, another component may be coupled to components 160 and/or 170, such as a tibial tray component 190 for an ankle replacement system similar to the tibial platform 12 described in reference to FIG. 17 of U.S. Pat. No. 8,715,362. Other components, such as one or of the tibia tray components described in U.S. patent application Ser. No. 17/650,116, may also be used. In some embodiments, the tibial tray component 190 may define a channel for receiving an artificial articular surface 191, which may be configured to engage another articular surface, such as a talus or another artificial articular surface 192, as shown in FIG. 1. In some embodiments, one of the stem components 160, 170, and/or 180 may be coupled to the tray component 190 by aligning spaced apart rails of the stem component 160, 170, and/or 180 with an engagement element disposed on the tray component 190 similar to the coupling described above for the coupling of components 160 and 170, 180. In other embodiments, tray component 190 may be coupled to another stem component 160, 170, and/or 180 with a tapered connection. In the embodiment with a tapered connection for the tray component 190, a modified stem component, such as component 160, 170, or 180, would be provided without the channel and spaced apart rails as described above and would be adapted to fit with the tapered connection of the tray component 190.

Component 170 may be decoupled from component 160 by removing the locking mechanism (e.g., removing the set screw if applicable) and pulling the component 170 forward (e.g., in an anterior direction) along the spaced apart rails 128*a*, 130*a* and 122*b*, 124*b* of both components 160, 170. In some embodiments, a removal tool (not shown) may be used to remove the locking mechanism or force the component 170 out of contact with the back end of the channel 126*a* as will be understood by one of ordinary skill in the art.

Component 180 may be decoupled from component 160 by removing the locking mechanism (e.g., removing the set screw if applicable) and pulling the component 160 forward (e.g., in an anterior direction) along the spaced apart rails 122*a*, 124*a* and 122*c*, 124*c* of both components 160, 180. In some embodiments, a removal tool (not shown) may be used to remove the locking mechanism or force the component 160 out of contact with the back end of the channel 126*c* as will be understood by one of ordinary skill in the art.

In some embodiments, the decoupling and removal of the tibial tray component 190, from at least one other component (e.g., component 160, 170, and/or 180) allows access to the internal engagement features of at least one other component 160, 170, 180. Removal of the tibial tray component 190, may be achieved with an impacting instrument(s) in a distal or caudal direction as will be understood by one of ordinary skill in the art. The internal engagement features of the components 160, 170, 180 may be spaced apart rails, such as the spaced apart rails 128*a*, 130*a* of component 160, and may be configured to engage a removal instrument (not shown). The removal instrument may engage the internal engagement features of components 160, 170, and/or 180, such as the spaced apart rails 128*a*, 130*a* of component 160, to facilitate removal. It is understood that the internal engagement features may also include holes, tabs, threads, and/or recesses to facilitate engagement with the removal instrument(s).

As best seen in FIGS. 6-9, stem components may include an extraction opening 132*a*, 132*b* in the body 102*a*, 102*b* configured to fit a separate tool, such as extraction tool 134, to allow for the decoupling and removal of at least one component, such as components 160, 170, and/or 180. In some embodiments, the extraction tool 134 may include a handle 136 disposed on a first end of the extraction tool 134 and an extraction mechanism 138 disposed on a second end of the extraction tool 134. The extraction mechanism 138, may in some embodiments, be a protrusion that extends at an angle from the shaft and adapted to fit inside of a recess 140*a*, 140*b* disposed inside of the extraction opening 132*a* 132*b* on body 102*a*, 102*b*. In some embodiments, the decoupling and removal of the stem components may include inserting the extraction tool 134 and extraction mechanism 138 into the extraction opening 132*a*, 132*b* and the recess 140*a*, 140*b* disposed on body 102*a*, 102*b*. Removal may then be facilitated by pulling away from (or in the posterior direction) the stem allowing the stem components to move along the spaced apart rails, such as spaced apart rails 128*a*, 130*a* and 122*b*, 124*b* of components 160 and 170 respectively.

FIGS. 10-22 illustrate another example of a system 200 having a coupling mechanism in accordance with some embodiments. In some embodiments, the system 200 may be an ankle prosthesis including a stem 250, a tibia tray component 190, a tibial artificial joint surface 191, a talar component 192 with artificial surface, and a talar stem 193. The stem 250 may be a multi-component stem including two or more components that may be coupled by a coupling mechanism, which may be a dovetail coupling mechanism, as described herein. Although the components described herein are described with reference to an ankle prosthesis, the components, systems, and methods are not so limited, as one of ordinary skill in the art will understand that the components may be adapted for other prosthesis, including the hip, knee, and shoulder, to list only a few possible examples.

Figure 11:
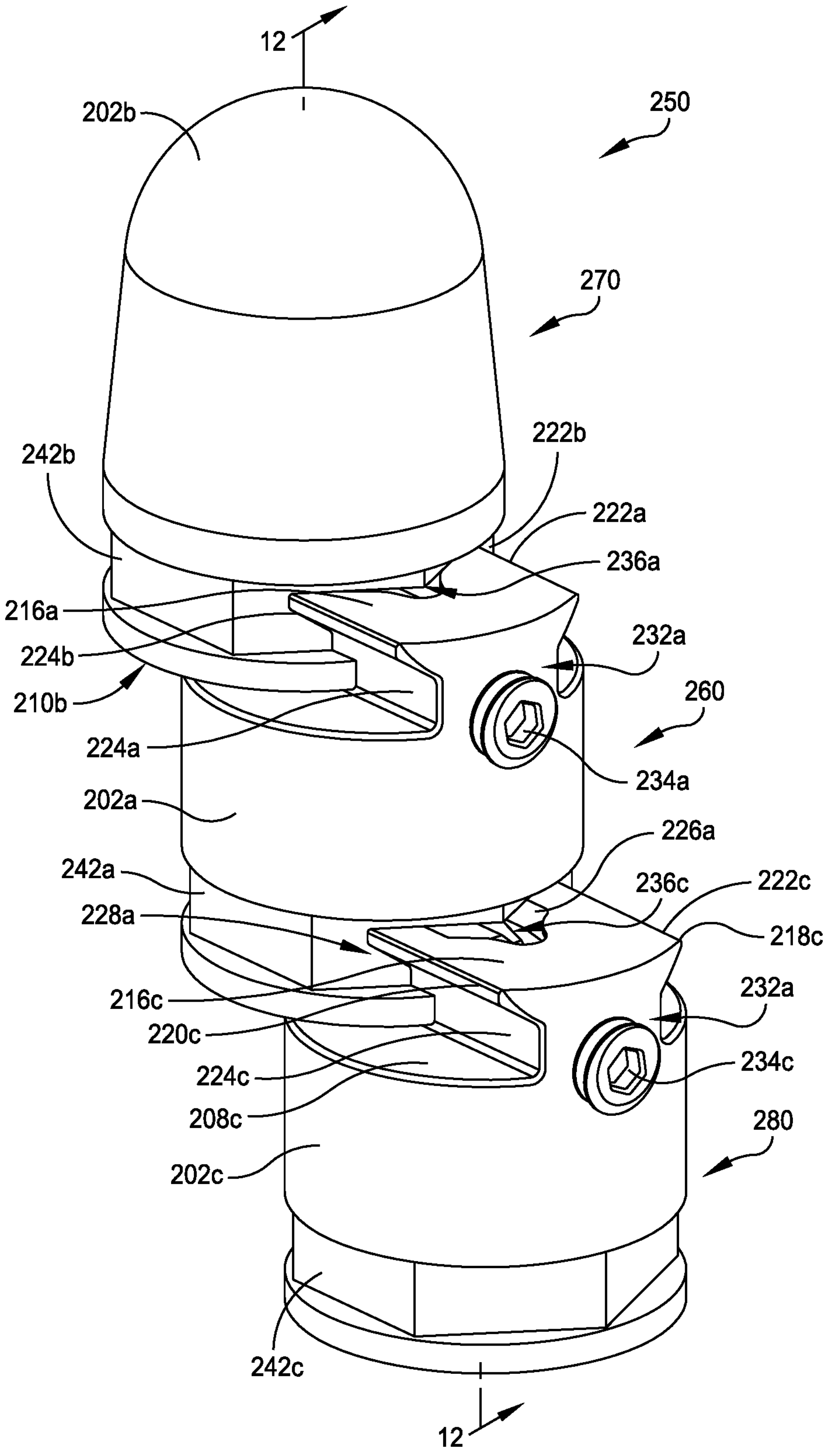
FIG. 11 is an isometric view of stem components illustrated in FIG. 10 in accordance with some embodiments.
Figure 12:
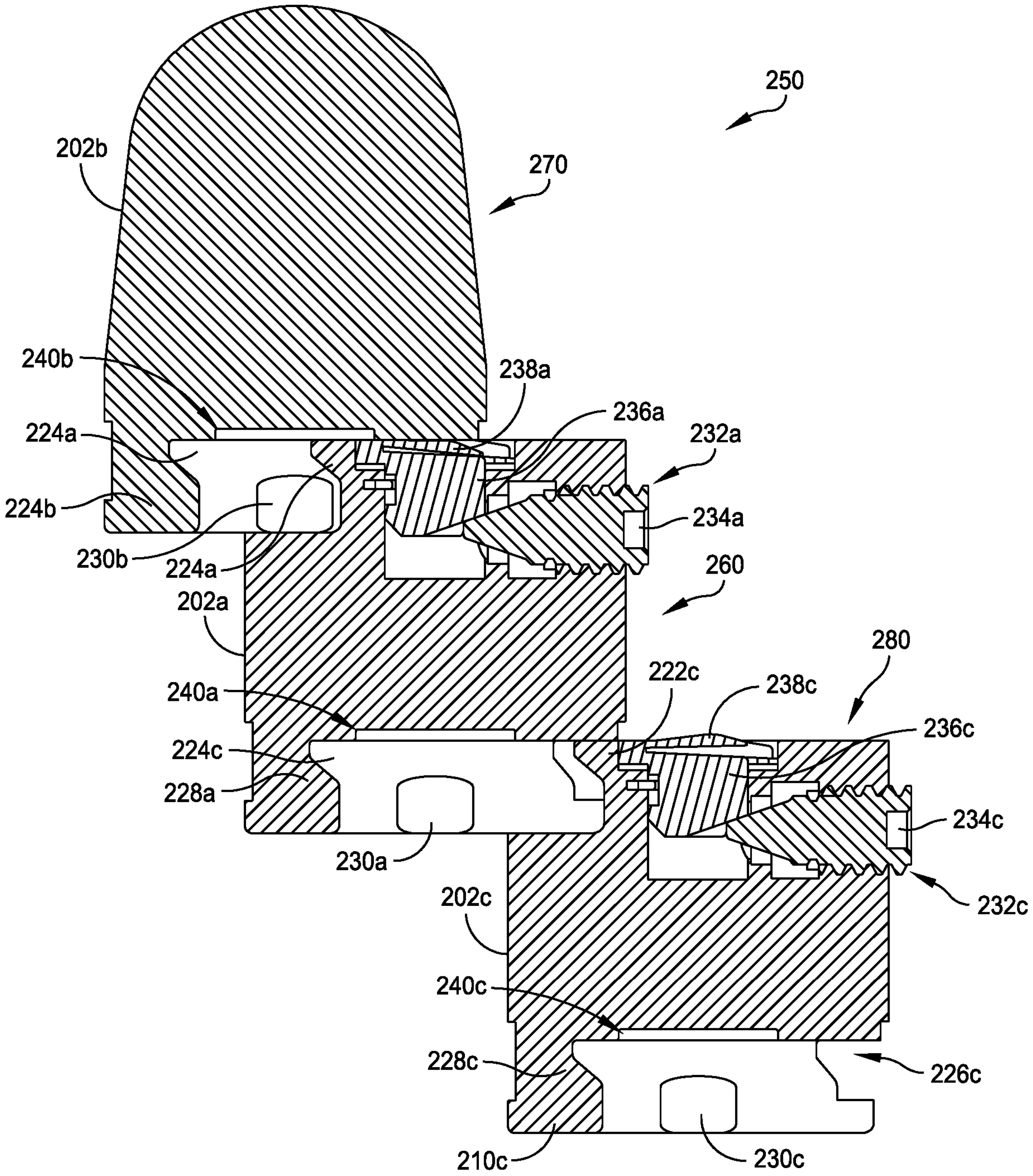
FIG. 12 is a cross-sectional view of stem components illustrated in FIG. 11 taken along line 12-12 in FIG. 11 in accordance with some embodiments.
Figure 13:
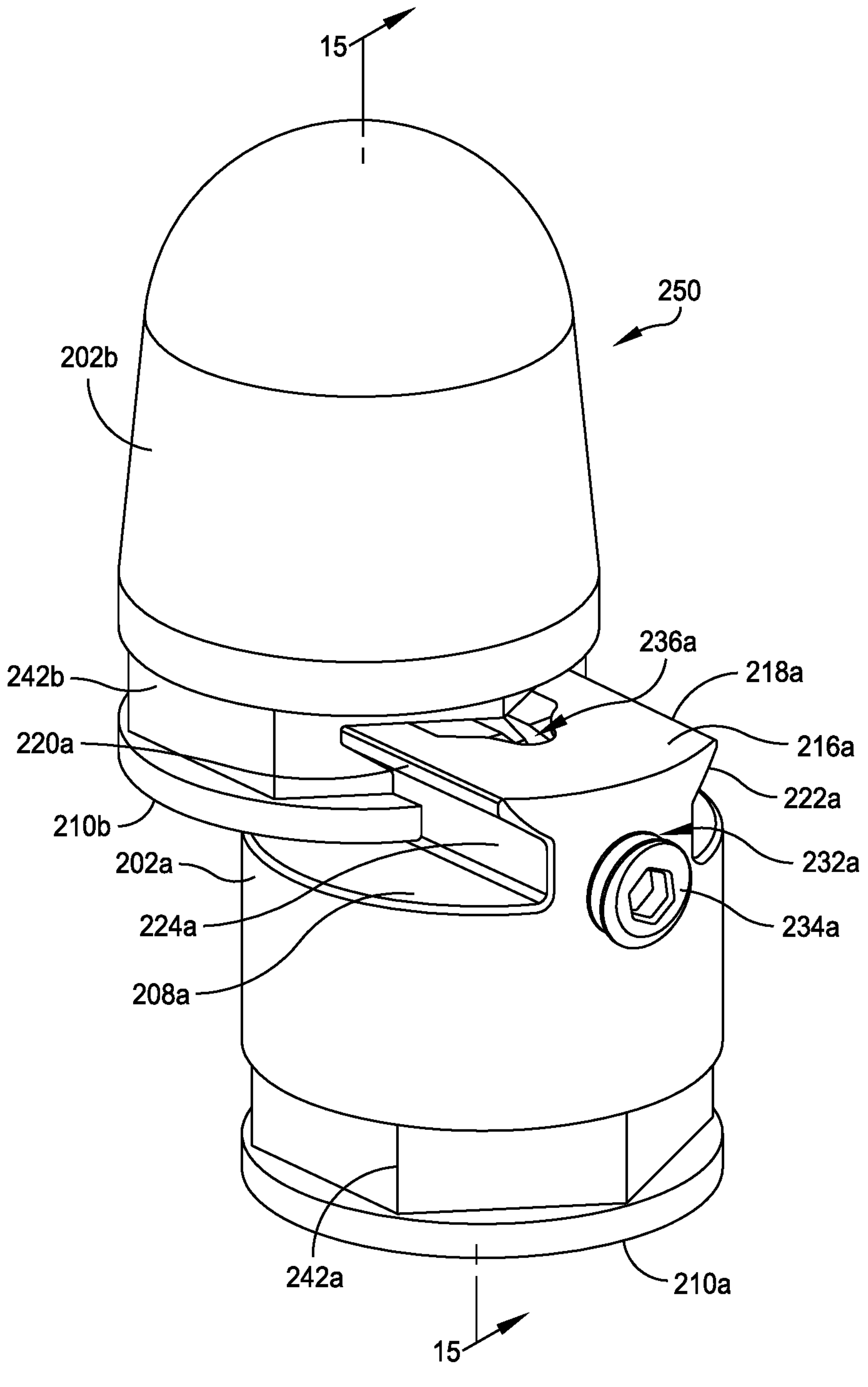
FIG. 13 is an isometric view of the top and the middle stem components of the system illustrated in FIG. 10 in accordance with some embodiments.
Figure 14:
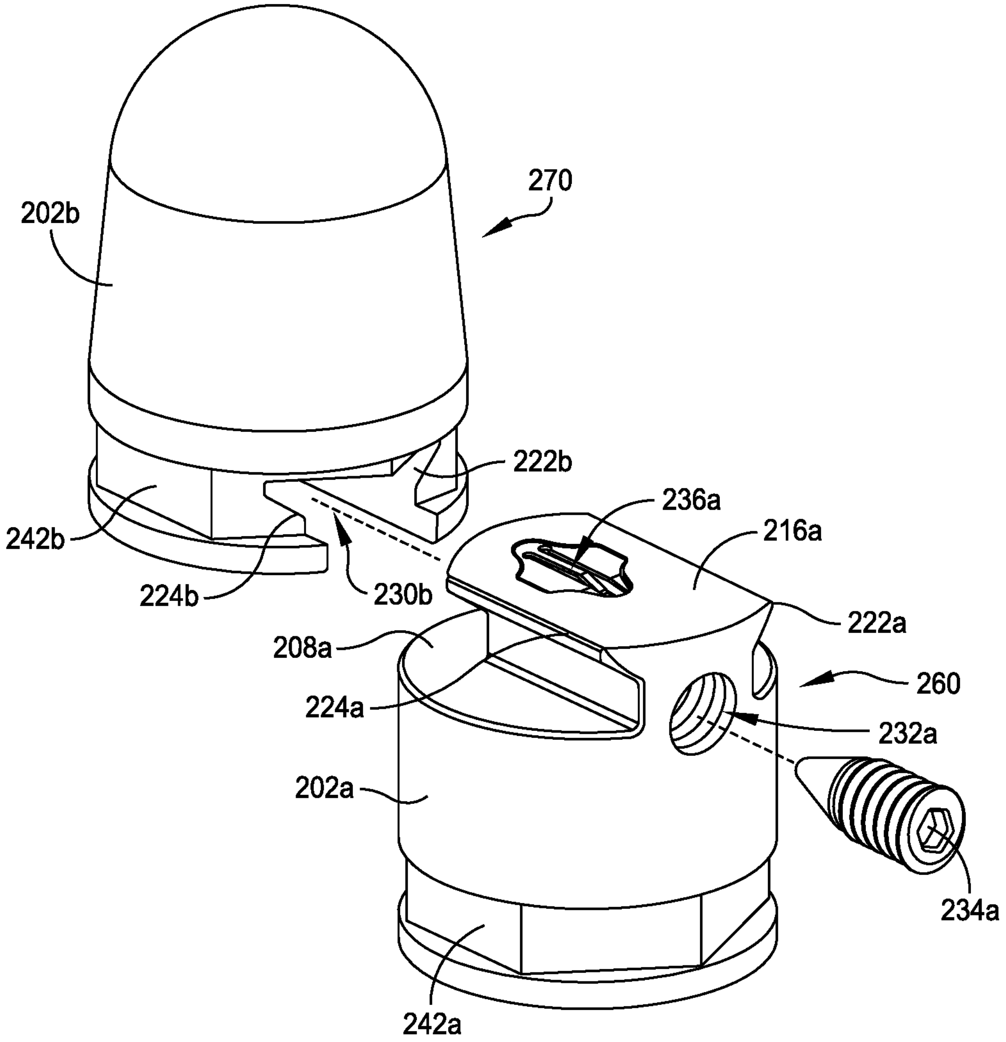
FIG. 14 is an exploded view of the stem components illustrated in FIG. 3 in accordance with some embodiments.
Figure 16:
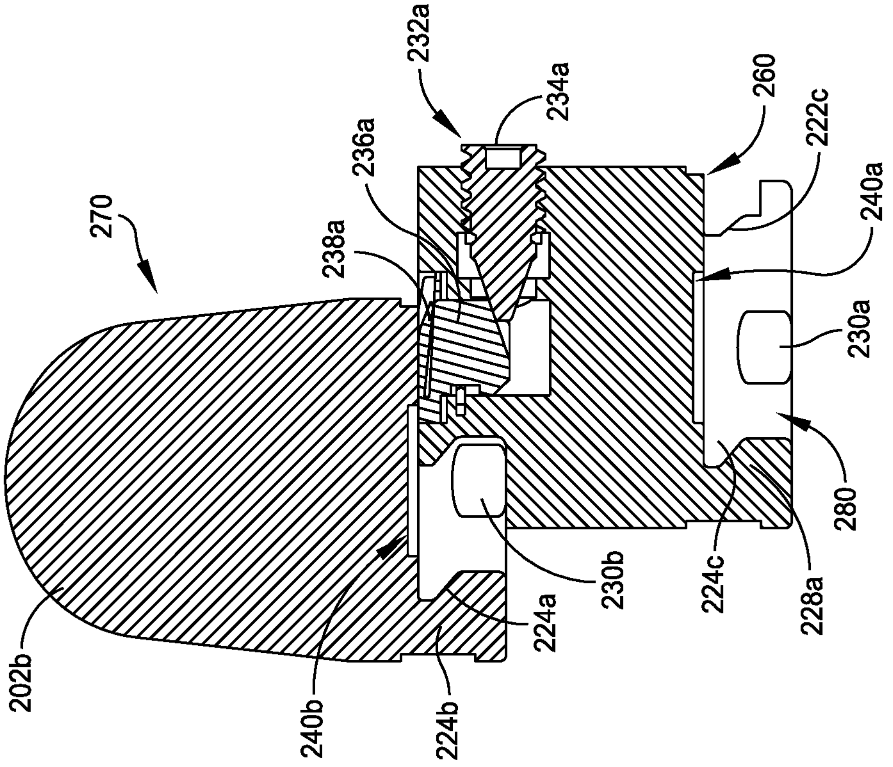
FIG. 16 is a cross-sectional view of the stem components illustrated in FIG. 13, in a second position, taken along line 15-15 in FIG. 13 in accordance with some embodiments.
Figure 15:
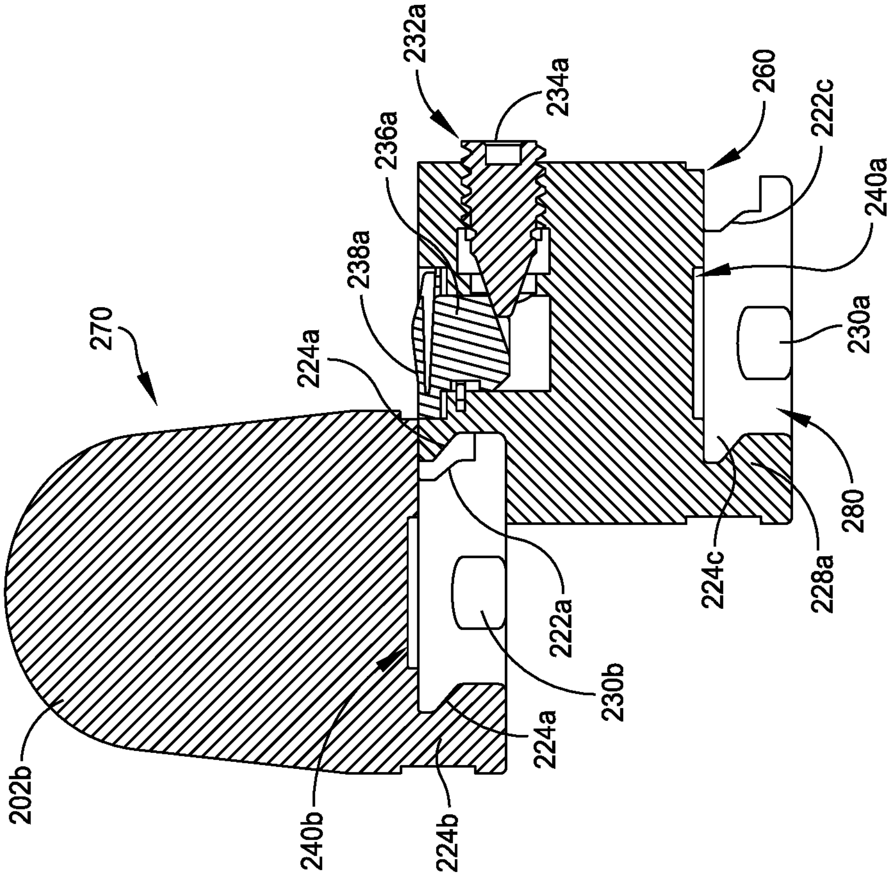
FIG. 15 is a cross-sectional view of the stem components illustrated in FIG. 13, in a first position, taken along line 15-15 in FIG. 13 in accordance with some embodiments.

In the example illustrated in FIG. 11, the stem 250 includes a first component 270, which may be a top or leading component, a second component 260, which may be a middle component, and a third component 280, which may be a bottom component or another middle component. It should be understood that the second and third components may be identical or different depending on the length and configuration of the stem, as described herein. In some embodiments, the components 260, 270, 280 that may be coupled together either in situ or ex situ.

Each of the stem components 260, 270, 280 may include a body 202*a*, 202*b*, 202*c* having generally a cylindrical shape, with stem component 270 tapering along its length from a first diameter at leading end to a second diameter at its trailing end. In some embodiments, the second diameter is greater than the first diameter. It should be understood that stem components 260, 270, 280 may have other shapes or configurations (e.g., pyramidal, cubic, and/or oval, to list only a few examples). In addition, the components 260, 270, and/or 280 could be arched to reduce and/or prevent rotation, and could be of constant or varying cross-sectional widths. In some embodiments, the stem components 260, 270, 280 may include one or more anti-rotation features extending radially outward from the body 202*a*, 202*b*, 202*c*, as will be understood by one of ordinary skill in the art. Examples of such anti-rotation features are described in U.S. Patent Application Publication No. 2022/0280307 and U.S. Provisional Application No. 63/374,248, filed Sep. 1, 2022, which are incorporated by reference herein in its entirety. The body of the components 260, 270, and/or 280 may be formed using an additive manufacturing process, such as Direct Metal Laser Sintering (DMLS) or Electron Beam Melting (EBM), to list only a few possibilities. Other conventional manufacturing processes, such as machining, molding, extruding, and combinations thereof, may also be used as will be understood by one of ordinary skill in the art.

In some embodiments, the body 202*b* of leading component 270 may further include a face 210*b*. The face 210*b* may define a pair of spaced apart rails 222*b* and 224*b*, disposed within channel 230*b*, configured to slide along spaced apart rails of another prosthesis component (e.g., stem component 160, 170 and/or another stem component of a multi-component stem) to form a dovetail coupling. The face 210*b* may further define a detent 240*b* adapted to engage a biasing member of another prosthesis component (e.g., stem component 160, 170 and/or another stem component of a multi-component stem) to lock the components together.

In some embodiments, the body 202*a* of stem component 260 may further include a first face 208*a* and a second face 210*a*. The first face 208*a* may, in some embodiments, define an engagement element 216*a*, such as a shelf or one or more flats, having a first edge 218*a* and a second edge 220*a*. The first 218*a* and second 220*a* edges define spaced apart rails 222*a* and 224*a* respectively, configured to slide along spaced apart rails within a channel disposed on the second face of another prosthesis component (e.g., prosthesis component 260, 280, and/or another stem component, such as leading component 270, of a multi-component stem) to form a dovetail coupling. The second face 210*a* may define a pair of spaced apart rails 226*a* and 228*a*, disposed within channel 230*a*, configured to slide along spaced apart rails of another prosthesis component (e.g., stem component 160, 170 and/or another stem component of a multi-component stem) to form a dovetail coupling. The second face 210*a* may further define a detent 240*a* adapted to engage a biasing member of another prosthesis component (e.g., stem component 260, 280 and/or another stem component of a multi-component stem) to lock the components together. One of ordinary skill in the art will understand that other engagement elements may be used instead of flats, rails, or shelfs.

In some embodiments, the body 202*a* of the prosthesis component 260 includes a securing mechanism 232*a*, wherein the securing mechanism is a hole extending inwardly from the outer surface perpendicular to longitudinal axis. The hole could be a blind hole or a through hole, and configured to receive a locking mechanism 234*a* at an angle perpendicular to the longitudinal axis of the body 202*a*. The securing mechanism 232*a* may comprise a threaded opening, partially threaded opening, and/or tapered opening, according to some embodiments. The locking mechanism 234*a* may include a fastener, such as a screw, clip, pin, bolt, nail, or plug just to give a few examples. The locking mechanism 234*a* may be threaded, partially threaded, and/or tapered to be compatible with the opening of the securing mechanism 232*a* as described above.

The body 202*a* may include a biasing member 236*a* on the first face 208*a* of the body 202*a*. According to some embodiments, the biasing member 236*a* may be configured to move along the longitudinal axis when in contact with the locking mechanism 234*a*. The biasing member is adapted to move into at least two positions to secure two components together. In further embodiments, the biasing member 236*a*, may include a clip 238*a* adapted to latch the first prosthesis component 260 with another prosthesis component (e.g., prosthesis component 260, 270, 280 and/or another stem component of a multi-component stem).

In some embodiments, the body 202*c* of stem component 270 may further include a first face 208*c* and a second face 210*c*. The first face 208*c* may, in some embodiments, define an engagement element 216*c*, such as a shelf or one or more flats, having a first edge 218*c* and a second edge 220*c*. The first 218*c* and second 220*c* edges define spaced apart rails 222*c* and 224*c* respectively, configured to slide along spaced apart rails within a channel disposed on the second face of another prosthesis component (e.g., prosthesis component 260, 280, and/or another stem component of a multi-component stem) to form a dovetail coupling. The second face 210*c* may define a pair of spaced apart rails 226*c* and 228*c*, disposed within channel 230*c*, configured to slide along spaced apart rails of another prosthesis component (e.g., stem component 160, 180 and/or another stem component of a multi-component stem) to form a dovetail coupling. The second face 210*c* may further define a detent 240*c* adapted to engage a biasing member of another prosthesis component (e.g., stem component 260, 280 and/or another stem component of a multi-component stem) to lock the components together. One of ordinary skill in the art will understand that other engagement elements may be used instead of flats, rails, or shelfs.

In some embodiments, the body 202*c* of the prosthesis component 280 includes a securing mechanism 232*c*, wherein the securing mechanism is a hole extending inwardly from the outer surface perpendicular to longitudinal axis. The hole could be a blind hole or a through hole, and configured to receive a locking mechanism 234*c* at an angle perpendicular to the longitudinal axis of the body 202*c*. The securing mechanism 232*c* may comprise a threaded opening, partially threaded opening, and/or tapered opening, according to some embodiments. The locking mechanism 234*c* may include a fastener, such as a screw, clip, pin, bolt, nail, or plug just to give a few examples. The locking mechanism 234*c* may be threaded, partially threaded, and/or tapered to be compatible with the opening of the securing mechanism 232*c* as described above.

The body 202*c* may include a biasing member 236*c* on the first face 208*c* of the body 202*c*. According to some embodiments, the biasing member 236*c* may be configured to move along the longitudinal axis when in contact with the locking mechanism 234*c*. The biasing member is adapted to move into at least two positions to secure two components together. In further embodiments, the biasing member 236*c*, may include a clip 238*c* adapted to latch the prosthesis component 280 with another prosthesis component (e.g., prosthesis component 260, 270, 280 and/or another stem component of a multi-component stem).

As best seen in FIGS. 15-18, a leading component 270, may be attached to components 260, 280. For example, the body 202*b* of component 270 may be inserted into a resected joint space between first and second bones, which may be a tibia and a talus. The component 270 may be advanced, at least partially, into an intramedullary canal form in one of the bones (e.g., the tibia). Component 260 may then be coupled to the component 270 by aligning spaced apart rails 222*a*, 224*a* and 222*b*, and 224*b* of the two components 260, 270. Once aligned component 260 may be pushed into engagement (e.g., by pushing in a first direction such as backward or in a posterior direction) so that engagement element 216*a* on the first face 208*a* of component 260 contacts the back end of the channel 230*b*. The locking mechanism 234*a*, such as a setscrew, may be installed in the securing mechanism 232*a* by hand and/or with an installation tool, according to some embodiments. When installed, the locking mechanism 232*a* pushes biasing member 236*a* into a detent 240*b* on the second face 210*b* of component 270 (or other compatible prosthesis component as discussed above). The clip 238*a* of the biasing member 236*a* may be used to lock the two components 260, 270 together once pushed into detent 240*b*. Stem component 260 may be installed by hand and/or by using a tool fitted around the body to install the two components 260, 270. One of ordinary skill in the art will understand that other engagement elements may be used, such as a spring-loaded detent or a depression and projections.

In some embodiments, the body 202*a*, 202*b*, 202*c* optionally includes a surface 242*a*, 242*b* configured to be engaged by a tool, such as a wrench, during the coupling of the first prosthesis component 260 to another component (e.g., to prosthesis component 270, 280 and/or to another stem component of a multi-component stem).

Bottom or middle component 280 may be coupled to middle component 260 by aligning spaced apart rails 226*a*, 228*a* and 222*c*, 224*c* for the two components 260 and 280. Once aligned, component 260 may be pushed into engagement (e.g., by pushing in a first direction such as backward) so that engagement element 216*c* contacts the back end of the channel 230*a*. Once component 280 is pushed into engagement, a locking mechanism 234*c* may be installed in the securing mechanism opening 232*c*. The installation of the locking mechanism 234*c* may push the biasing member 236*c* and clip 238*c* into the detent 240*a* locking the two components together and completing the coupling. In some embodiments, the body 202*c* includes a surface 242*c* configured to be engaged by a tool, such as a wrench, during the coupling of the prosthesis component 280 to another component (e.g., to first prosthesis component 260 and/or to another stem component of a multi-component stem).

Figure 10:
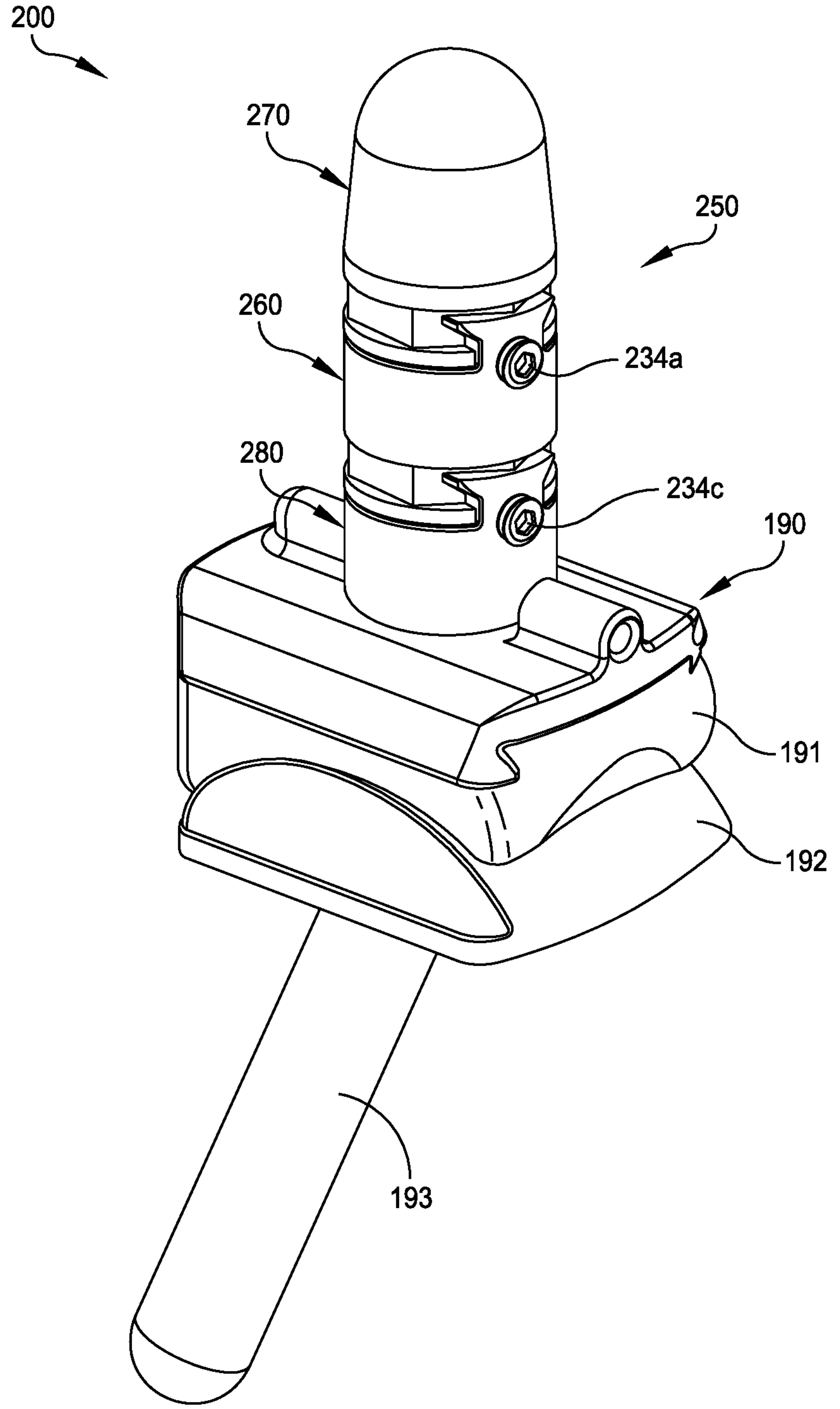
FIG. 10 is an isometric view of an example of a prosthesis system having a coupling mechanism in accordance with some embodiments.

In some embodiments, another component may be coupled to components 260, 270, or 280, such as a tibial tray component 190 for an ankle replacement system similar to the tibial platform 12 described in reference to FIG. 17 of U.S. Pat. No. 8,715,362. Other components, such as one or of the tibia tray components 190 described in U.S. patent application Ser. No. 17/650,116, may also be used. In some embodiments, the tibial tray component 190 may define a channel for receiving an artificial articular surface 191, which may be configured to engage another articular surface, such as a talus or another artificial articular surface 192, as shown in FIG. 10. In some embodiments, one of the stem components 260, 270, and/or 280 may be coupled to the tray component 190 by aligning spaced apart rails of the stem component 260, 270, and/or 280 with an engagement element disposed on the tray component 190 similar to the dovetail coupling described above for the coupling of components 260 and 270, 280. In other embodiments, tray component 190 may be coupled to another stem component 260, 270, and/or 280 with a tapered connection. In the embodiment with a tapered connection for the tray component 190, a modified stem component, such as component 260, 270, or 280, would be provided without the channel and spaced apart rails as described above and would be adapted to fit with the tapered connection of the tray component 190.

Component 260 may be decoupled from component 270 by uninstalling the locking mechanism 234*a* and pulling the component 260 forward along the spaced apart rails 222*a*, 224*a* and 222*b*, 224*b* of both components. In some embodiments, a removal tool may be used to remove the locking mechanism 234*a* or force the component 260 out of contact with the back end of the channel 230*b* as will be understood by one of ordinary skill in the art. By uninstalling the locking mechanism 234*a*, the biasing member 236*a* and clip 238*a* are removed from the detent 240*b* unlocking the two components 260, 270 from each other and allowing the components to be slid apart on the spaced apart rails 222*a*, 224*a* and 222*b*, 224*b*.

The decoupling of components 260 and 280 may work in the same manner as the decoupling of components 260 and 270 described above. For example, component 260 may be decoupled from component 280 by uninstalling the locking mechanism 234*c* and pulling the component 280 forward (e.g., in an anterior direction) along the spaced apart rails 226*a*, 228*a* and 222*c*, 224*c* of both components. In some embodiments, a removal tool (not shown) may be used to remove the locking mechanism 234*c* or force the component 260 out of contact with the back end of the channel 230*a* as will be understood by one of ordinary skill in the art. By uninstalling the locking mechanism 234*c*, the biasing member 236*c* and clip 238*c* are removed from the detent 240*a* unlocking the two components 260 and 280 from each other and allowing the components to be slid apart on the spaced apart rails 226*a*, 228*a* and 222*c*, 224*c*.

In some embodiments, the decoupling and removal of the tibial tray component 190, from at least one other component (e.g., component 260, 270, and/or 280) allows access to the internal engagement features of at least one other component 260, 270, 280. Removal of the tibial tray component 190, may be achieved with an impacting instrument(s) in a distal or caudal direction as will be understood by one of ordinary skill in the art. The internal engagement features of the components 260, 270, 280 may be spaced apart rails, such as the spaced apart rails 226*a*, 228*a* of component 260, and may be configured to engage a removal instrument (not shown). The removal instrument may engage the internal engagement features of components 260, 270, and/or 280, such as the spaced apart rails 226*a*, 228*a* of component 260, to facilitate removal. It is understood that the internal engagement features may also include holes, tabs, threads, and/or recesses to facilitate engagement with the removal instrument(s).

As best seen in FIGS. 19-22, stem components may include an extraction opening 244*a*, 244*c* in the body 202*a*, 202*c* configured to fit a separate tool, such as extraction tool 134, to allow for the decoupling and removal of at least one component, such as components 260, 270, and/or 280. In some embodiments, the extraction tool 134 may include a handle 136 disposed on a first end of the extraction tool 134 and an extraction mechanism 138 disposed on a second end of the extraction tool 134. The extraction mechanism 138, may in some embodiments, be a protrusion that extends at an angle from the shaft and adapted to fit inside of a recess 246*a*, 246*c* disposed inside of the extraction opening 244*a* 244*c* on body 202*a*, 202*c*. In some embodiments, the decoupling and removal of the stem components may include inserting the extraction tool 134 and extraction mechanism 138 into the extraction opening 244*a*, 244*c* and a recess 246*a*, 246*c* disposed on body 202*a*, 202*c*. Removal may then be facilitated by pulling away from (or in the posterior direction) the stem allowing the stem components to move along the spaced apart rails, such as spaced apart rails 226*a*, 228*a* and 222*c*, 224*c* of components 160 and 170 respectively.

FIGS. 23-33 illustrate another example of a system 300 having a coupling mechanism in accordance with some embodiments. In some embodiments, the system 300 may be an ankle prosthesis including a stem 350, a tibia tray component 190, a tibial artificial joint surface 191, a talar component 192 with artificial surface, and a talar stem 193. The stem 350 may be a multi-component stem including two or more components that may be coupled by a coupling mechanism, which may be a dovetail coupling mechanism, as described herein. Although the components described herein are described with reference to an ankle prosthesis, the components, systems, and methods are not so limited, as one of ordinary skill in the art will understand that the components may be adapted for other prosthesis, including the hip, knee, and shoulder, to list only a few possible examples.

Figure 24:
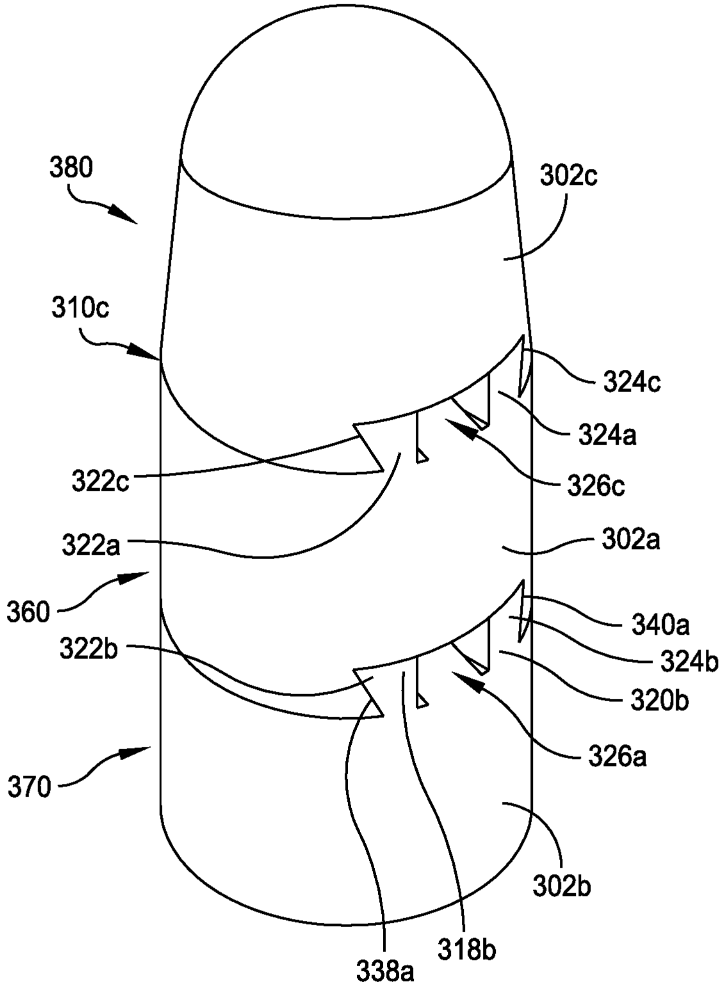
FIG. 24 is an isometric view of the stem components of the system illustrated in FIG. 23 in accordance with some embodiments.
Figure 25:
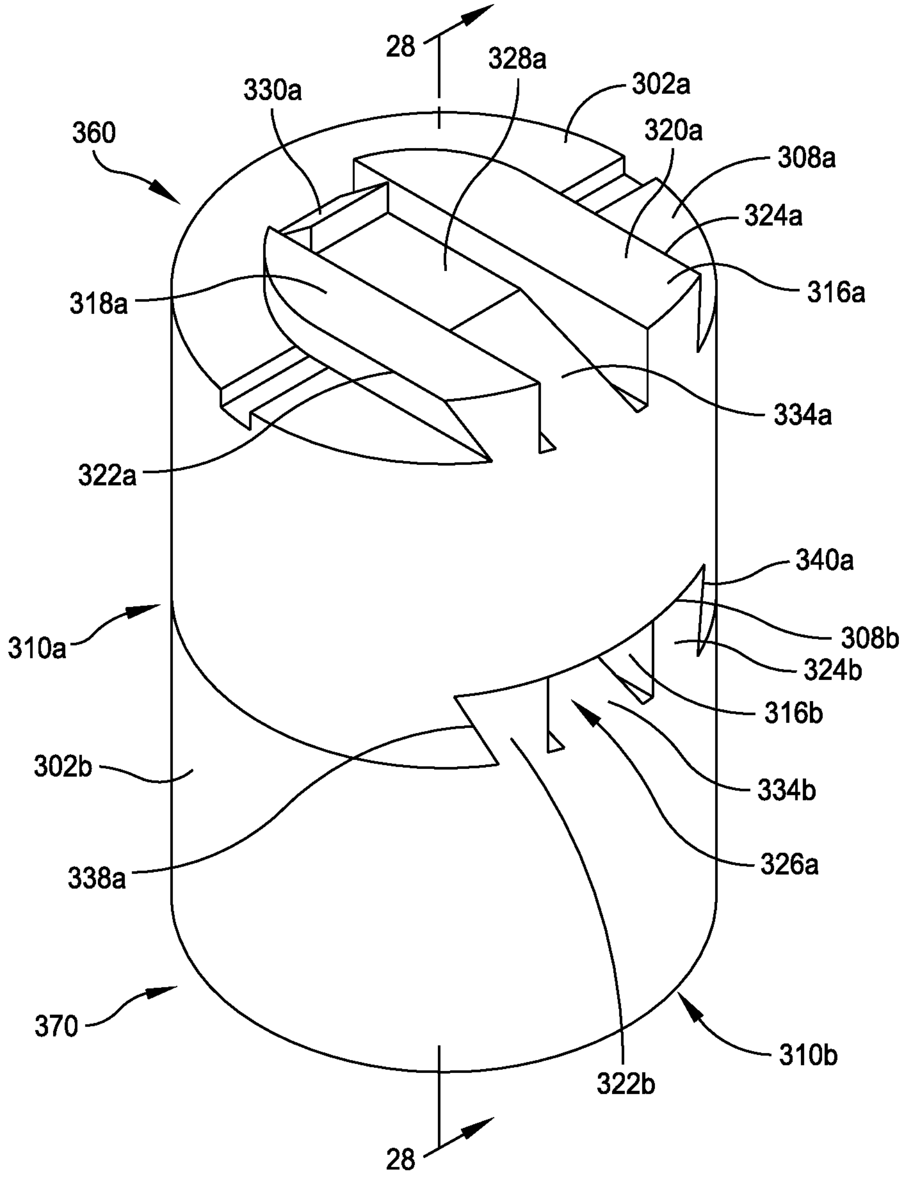
FIG. 25 is an isometric view of stem components of the system illustrated in FIG. 23 in accordance with some embodiments.
Figure 26:
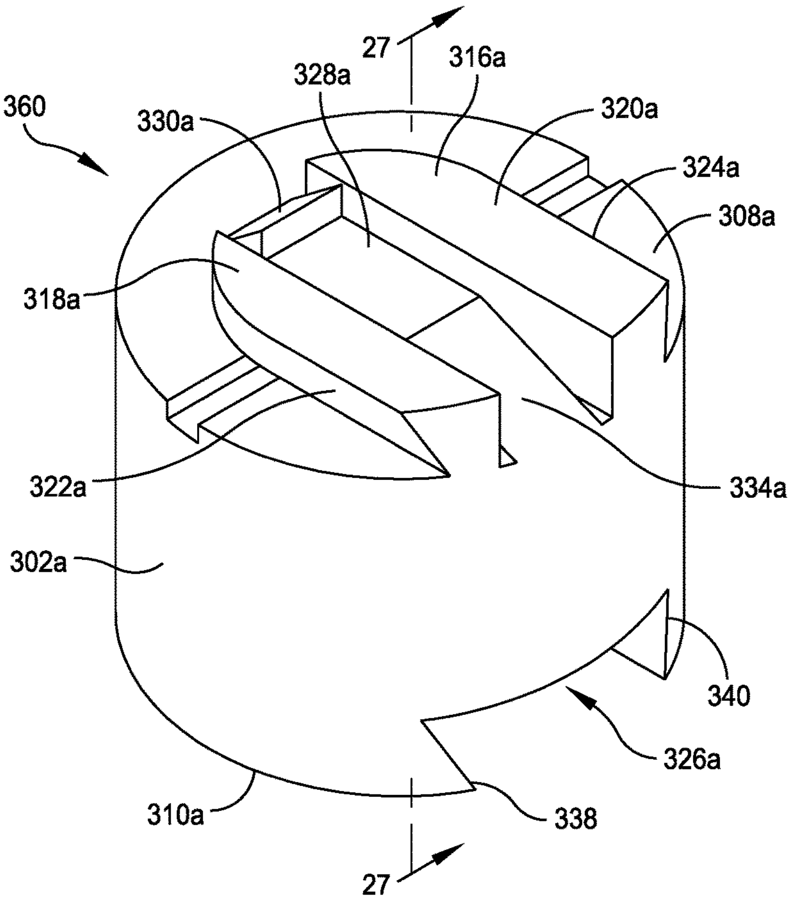
FIG. 26 is an isometric view of the middle stem component of the system illustrated in FIG. 23 in accordance with some embodiments.
Figure 27:
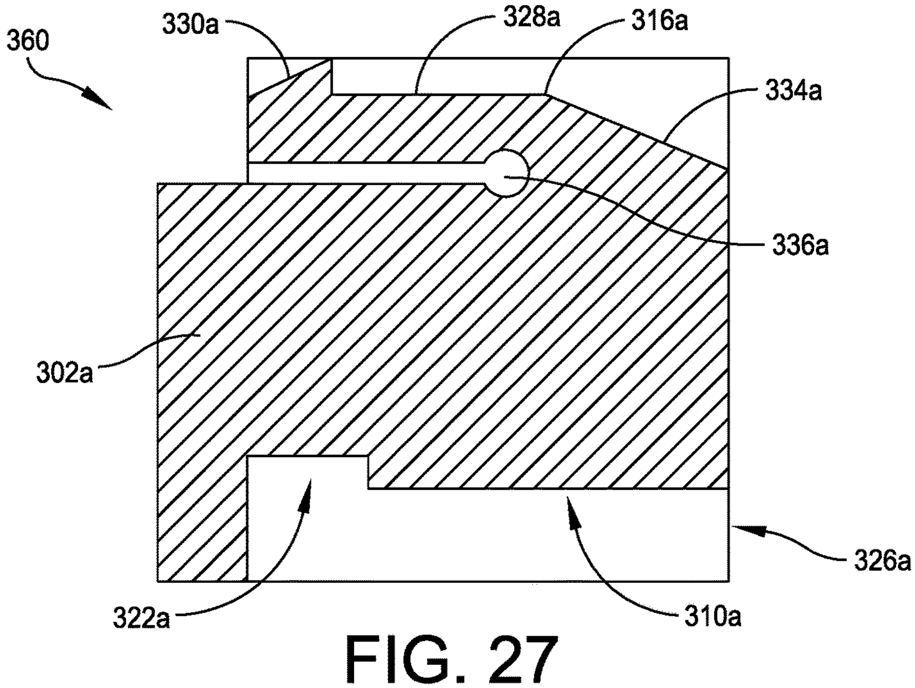
FIG. 27 is a cross-sectional view of the stem component illustrated in FIG. 26 taken along line 27-27 in FIG. 26 in accordance with some embodiments.
Figure 28:
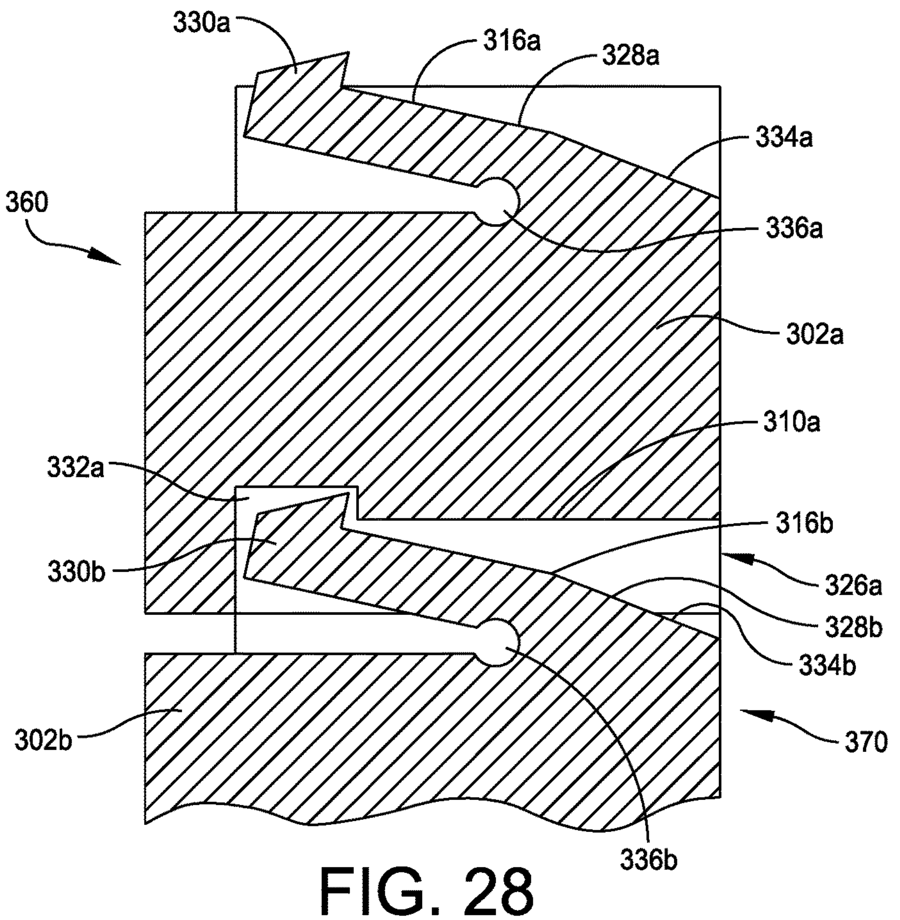
FIG. 28 is a cross-sectional view of the stem components illustrated in FIG. 25 taken along line 28-28 in FIG. 25 in accordance with some embodiments.
Figure 29:
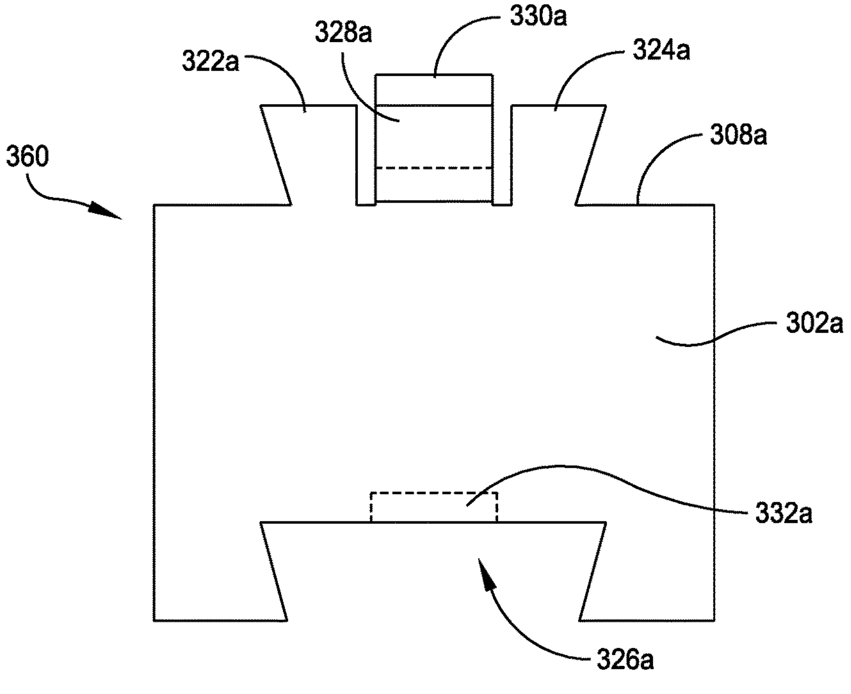
FIG. 29 is a side perspective view of the stem component illustrated in FIG. 26 according to some embodiments.
Figure 30:
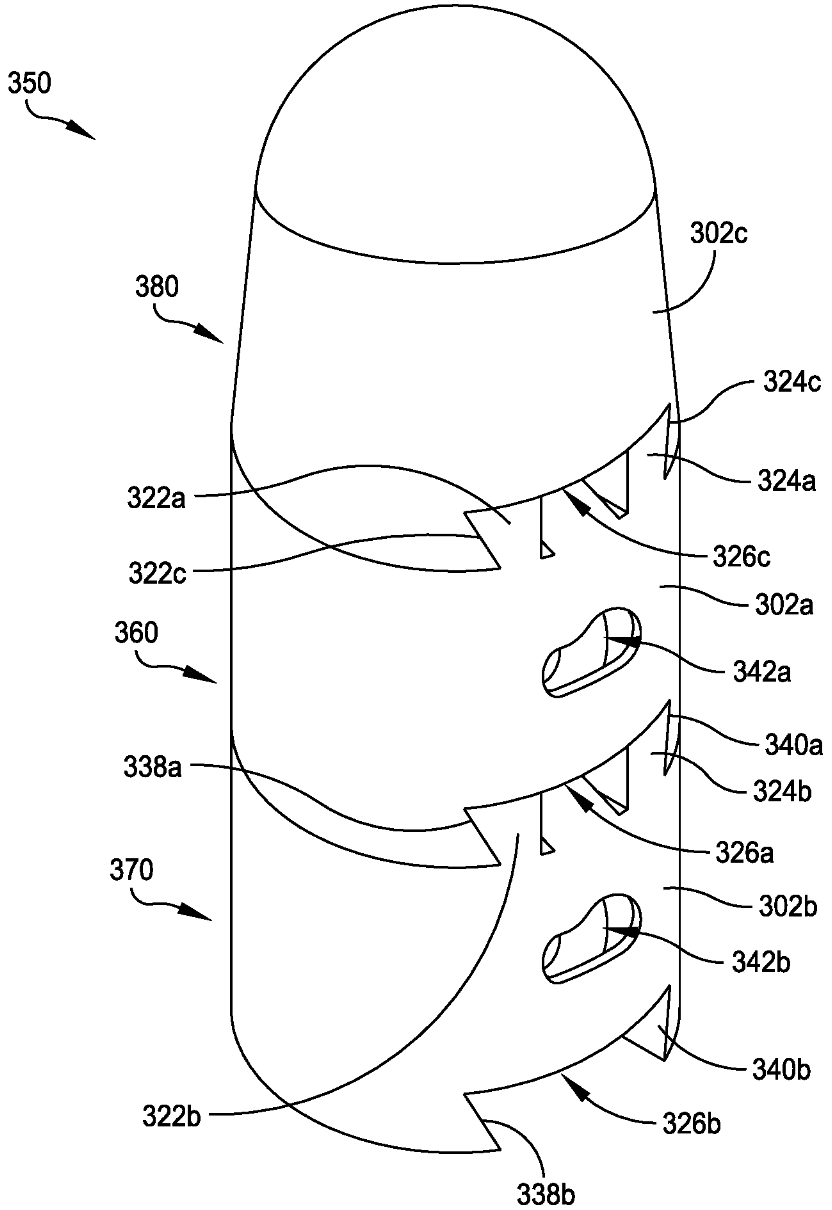
FIG. 30 is an isometric view of stem components of the system illustrated in FIG. 23 configured to allow removal with an extraction tool in accordance with some embodiments.
Figure 31:
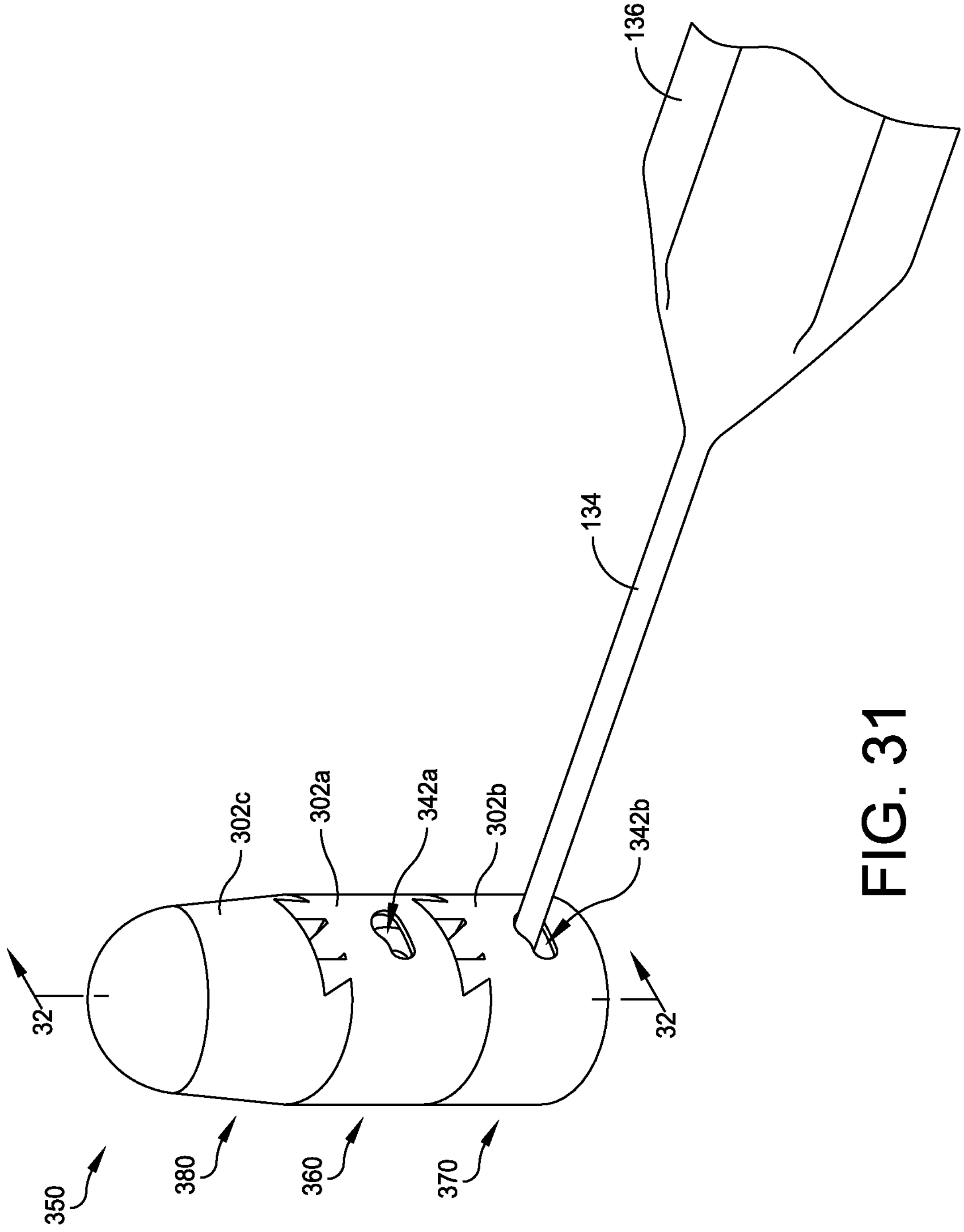
FIG. 31 is an isometric view of stem components of the system illustrated in FIG. 30 including an extraction tool in accordance with some embodiments.
Figure 32:
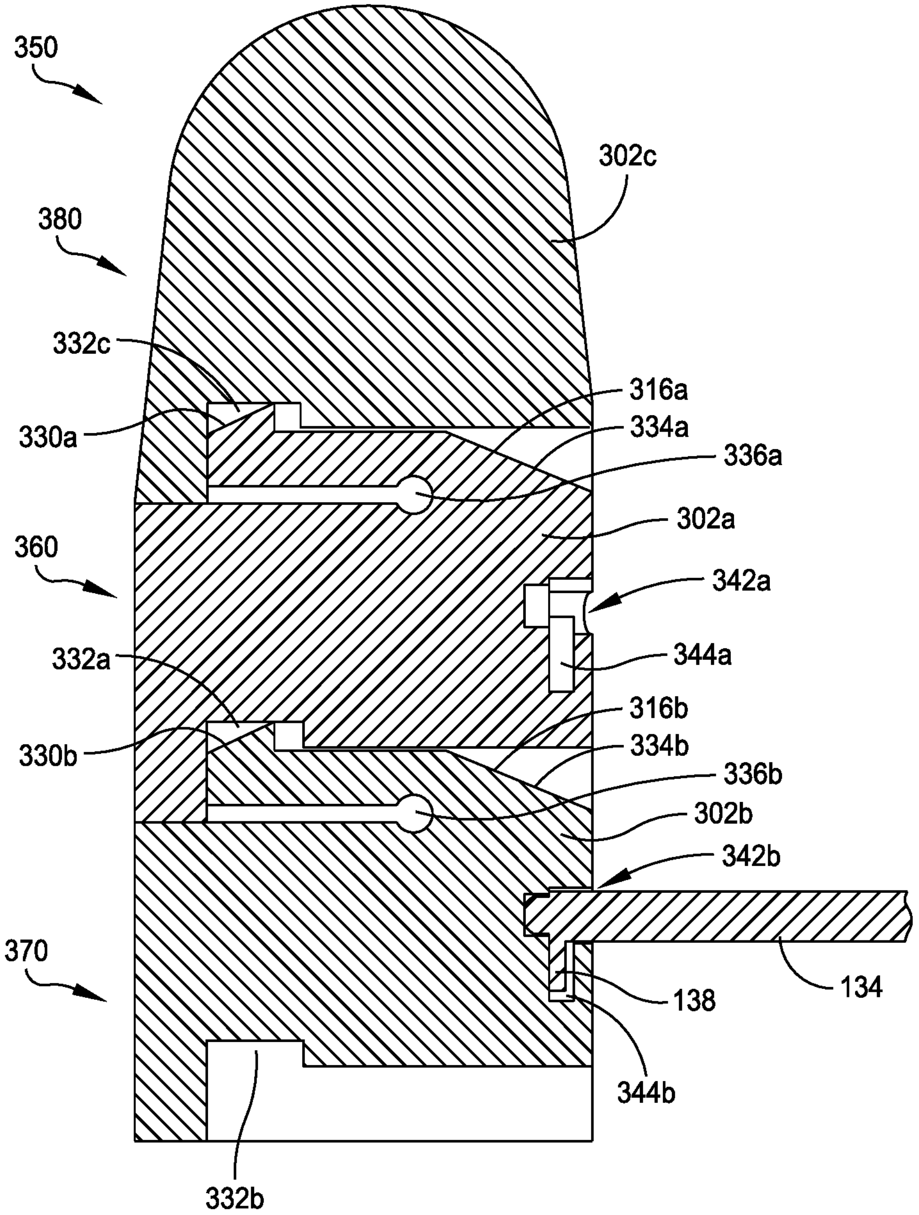
FIG. 32 is a cross-sectional view of stem components illustrated in FIG. 31, in a first position, taken along line 32-32 in FIG. 31 in accordance with some embodiments.
Figure 33:
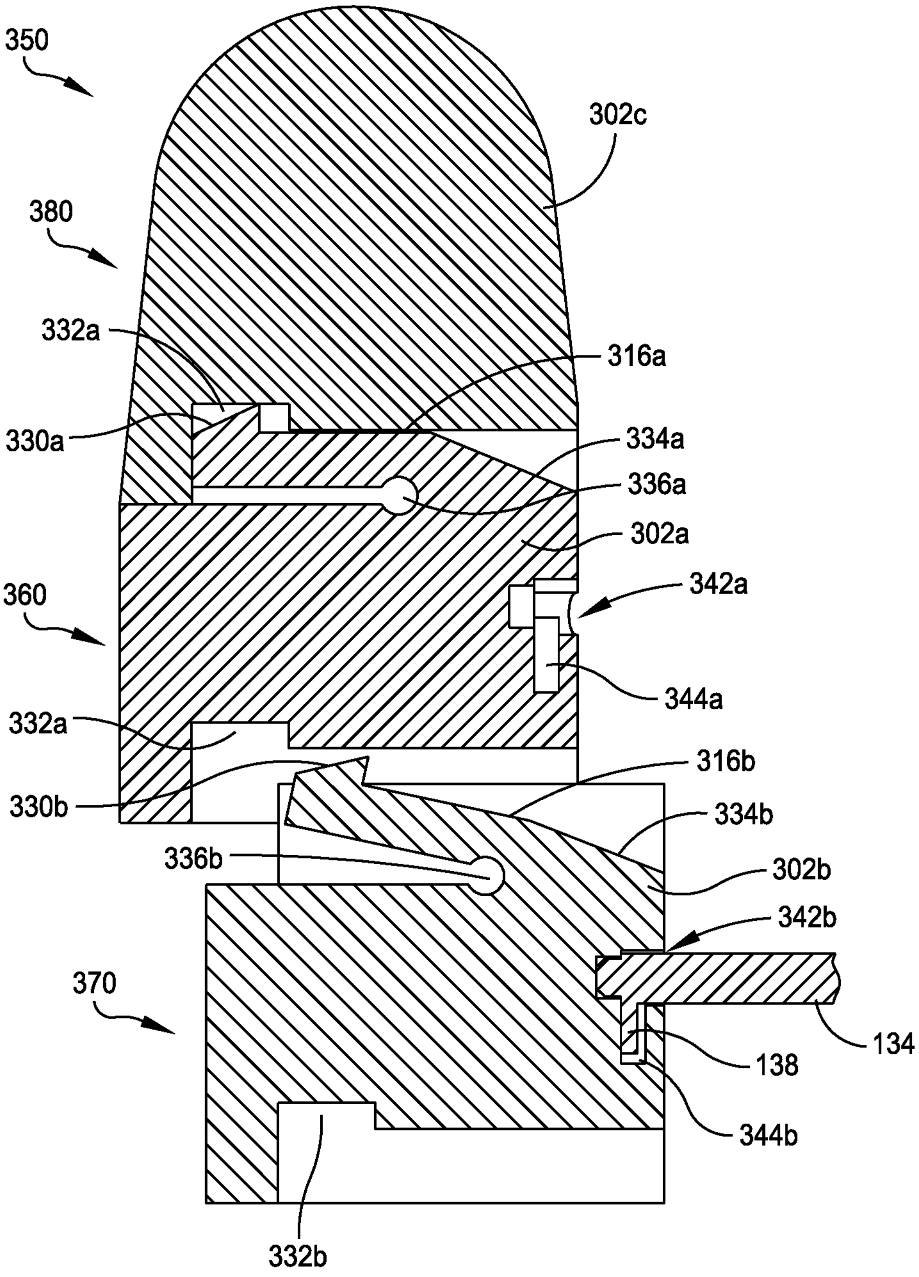
FIG. 33 is a cross-sectional view of stem components illustrated in FIG. 31, in a second position, taken along line 32-32 in FIG. 31 in accordance with some embodiments.

In the example illustrated in FIG. 24, the stem 350 includes a first component 380, which may be a top or leading component, a second component 360, which may be a middle component, and a third component 370, which may be a bottom or another middle component. It should be understood that the second and third components may be identical or different depending on the length and configuration of the stem, as described herein. In some embodiments, the components 360, 370, 380 may be coupled together either in situ or ex situ.

Each of the stem components 360, 370, 380 may include a body 302*a*, 302*b*, 302*c* having a generally cylindrical shape, with stem component 380 tapering along its length from a first diameter at leading end to a second diameter at its trailing end. In some embodiments, the second diameter is greater than the first diameter. It should be understood that stem component 360 may have other shapes or configurations (e.g., pyramidal, cubic, and/or oval, to list only a few examples). In addition, the stem components 360, 370, 380 could be arched to reduce and/or prevent rotation, and could be of constant or varying cross-sectional widths. In some embodiments, the stem components 360, 370, 380 may include one or more anti-rotation features extending radially outward from the body 302*a*, 302*b*, 302*c*, as will be understood by one of ordinary skill in the art. Examples of such anti-rotation features are described in U.S. Patent Application Publication No. 2022/0280307 and U.S. Provisional Application No. 63/374,248, filed Sep. 1, 2022, which are incorporated by reference herein in its entirety. Body 302*a*, 302*b*, 302*c* may be formed using an additive manufacturing process, such as Direct Metal Laser Sintering (DMLS) or Electron Beam Melting (EBM), to list only a few possibilities. Other conventional manufacturing processes, such as machining, molding, extruding, and combinations thereof, may also be used as will be understood by one of ordinary skill in the art.

In some embodiments, body 320*c* of leading component 380 further include a face 310*c*. The face 310*c* may define a pair of spaced apart rails 322*c* and 324*c*, disposed within channel 326*c*, configured to slide along spaced apart rails of another prosthesis component (e.g., stem component 360, 370 and/or another stem component of a multi-component stem) to form a dovetail coupling.

In some embodiments, the body 302*a* of the prosthesis component 360 may further include a first face 308*a* and a second face 310*a*. The first face 308*a* may, in some embodiments, define an engagement element 316*a* having a first edge 318*a* and a second edge 320*a*. The first 318*a* and second 320*a* edges include spaced apart rails 322*a* and 324*a* configured to slide along spaced apart rails of another prosthesis component (e.g., prosthesis component 360, 370 and/or another stem component, such as leading component 380, of a multi-component stem) to form a dovetail coupling. One of ordinary skill in the art will understand that other engagement elements may be used instead of flats, rails, or shelfs.

In some embodiments, body 302*a* further includes a biasing mechanism 328*a*, which may include a tab 330*a* configured to fit inside of a detent on the second face of another prosthesis component (e.g., prosthesis component 360, 370 and/or another stem component, such as leading component 380, of a multi-component stem). The engagement element 316*a* may also include an angled slope 334*a* configured to allow a removal tool (not shown), such as a flat head screwdriver, access to release the tab 330*a*. In some embodiments, the tab 330*a* and body 302*a* define a cut out 336*a* allowing the tab to move in the longitudinal direction. This movement by the tab 330*a* provides the ability for the tab 330*a* to fit into a detent, such as detent 332*b* on component 370 or a detent of component 380, during one example of the coupling process or to decouple the two components with the removal tool. In some embodiments, the cut out 336*a* may be circular in shape, but it should be understood that the cut out 336*a* may have other shapes (e.g., pyramidal, cubic, rectangular and/or oval, to list only a few examples).

In some embodiments, the body 302*b* of the prosthesis component 370 may further include a first face 308*b* and a second face 310*b*. The first face 308*b* may, in some embodiments, define an engagement element 316*b* having a first edge 318*b* and a second edge 320*b*. The first 318*b* and second 320*b* edges include spaced apart rails 322*b* and 324*b* configured to slide along spaced apart rails of another prosthesis component (e.g., prosthesis component 360, 370 and/or another stem component, such as leading component 380, of a multi-component stem) to form a dovetail coupling. One of ordinary skill in the art will understand that other engagement elements may be used instead of flats, rails, or shelfs.

In some embodiments, body 302*b* further includes a biasing mechanism 328*b*, which may include a tab 330*b* configured to fit inside of a detent of another prosthesis component (e.g., prosthesis component 360, 370 and/or another stem component, such as leading component 380, of a multi-component stem). The engagement element 316*b* may also include an angled slope 334*b* configured to allow a removal tool (not shown), such as a flat head screwdriver, access to release the tab 330*b*. In some embodiments, the tab 330*b* and body 302*b* define a cut out 336*b* allowing the tab to move in the longitudinal direction. This movement by the tab 330*b* provides the ability for the tab 330*b* to fit into a detent, such as detent 332*a* on component 360, during one example of the coupling process or to decouple the two components with the removal tool. In some embodiments, the cut out 336*b* may be circular in shape, but it should be understood that the cut out 336*b* may have other shapes (e.g., pyramidal, cubic, rectangular and/or oval, to list only a few examples).

In some embodiments, a leading component 380, may be attached to components 360 and/or 370. For example, the body 302*c* of component 380 may be inserted into a resected joint space between first and second bones, which may be a tibia and a talus. The component 380 may be advanced, at least partially, into an intramedullary canal form in one of the bones (e.g., the tibia). Component 360 may then be coupled to the component 380 by aligning spaced apart rails 322*a*, 324*a* and 322*c*, and 324*c* of the two components 360, 380. Once aligned, component 360 may be pushed into engagement (e.g., by pushing in a first direction such as backward or in a posterior direction) so that engagement element 316*a* on the first face 308*a* of component 360 contacts the back end of the channel 326*c*. Once component 360 is pushed into engagement, the tab 330*a* of the biasing mechanism 328*a* snaps into the detent, similar to detent 332*a*, 332*b*, (not shown) completing the coupling of components 360, 380.

Bottom or middle component 370 may be coupled to component 360 by aligning the spaced apart rails 338*a*, 340*a* and 322*b*, 324*b* for the two components 360, 370. Once aligned, component 370 may be pushed into engagement (e.g., by pushing in a first direction such as backward or posterior direction) so that engagement element 316*b* contacts the back end of the channel 326*a*. Once component 370 is pushed into engagement, the tab 330*b* of the biasing mechanism 328*b* snaps into the detent 332*a* completing the coupling of components 360, 380.

Figure 23:
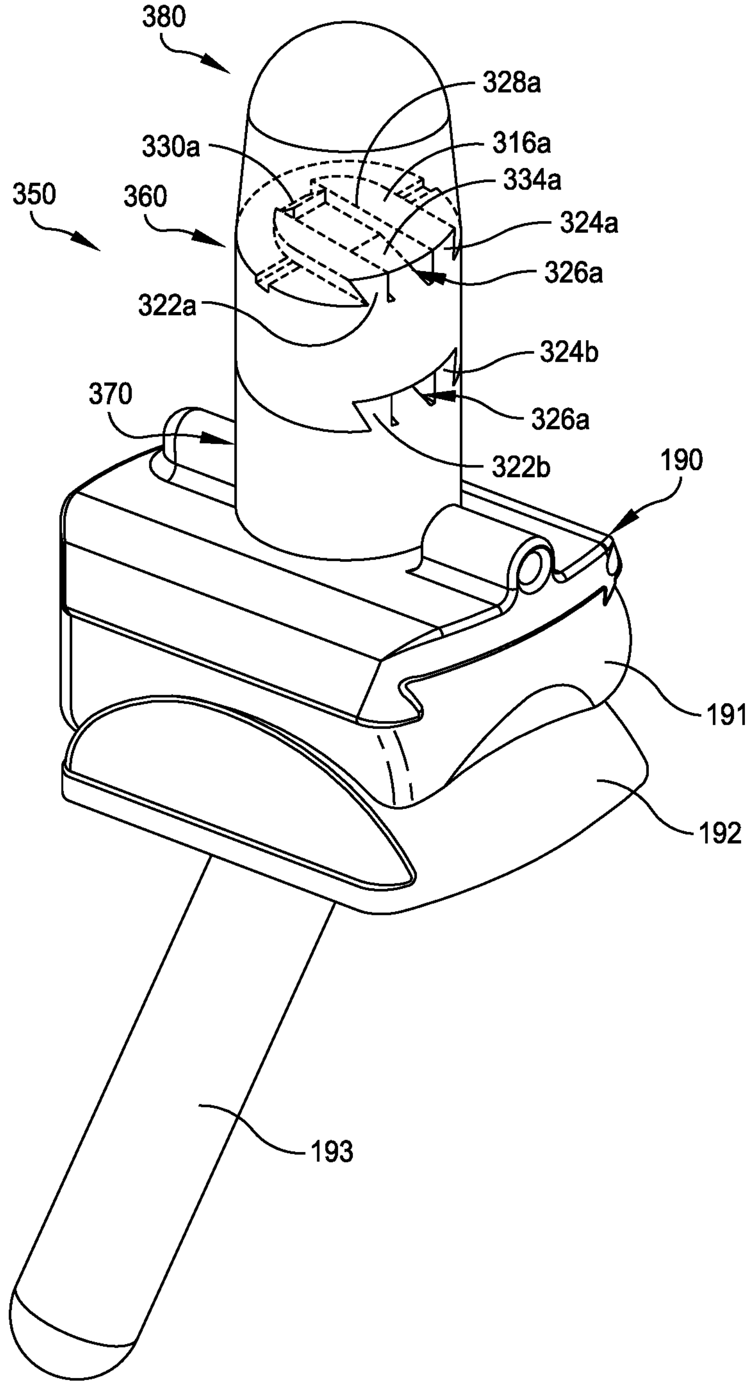
FIG. 23 is an isometric view of an example of a prosthesis system having a coupling mechanism in accordance with some embodiments.

In some embodiments, another component may be coupled to components 360, 370, or 380, such as a tibial tray component 190 for an ankle replacement system similar to the tibial platform 12 described in reference to FIG. 17 of U.S. Pat. No. 8,715,362. Other components, such as one or of the tibia tray components 190 described in U.S. patent application Ser. No. 17/650,116, may also be used. In some embodiments, the tibial tray component 190 may define a channel for receiving an artificial articular surface 191, which may be configured to engage another articular surface, such as a talus or another artificial articular surface 192, as shown in FIG. 23. In some embodiments, one of the stem components 360, 370, and/or 380 may be coupled to the tray component 190 by aligning spaced apart rails of the stem component 360, 370, and/or 380 with an engagement element disposed on the tray component 190 similar to the dovetail coupling described above for the coupling of components 360 and 370, 380. In other embodiments, tray component 190 may be coupled to another stem component 360, 370, and/or 380 with a tapered connection. In the embodiment with a tapered connection for the tray component 190, a modified stem component, such as component 360, 370, or 380, would be provided without the channel and spaced apart rails as described above and would be adapted to fit with the tapered connection of the tray component 190

Component 370 may be decoupled from component 360 by inserting a removal tool (not shown) along the angled slope 334*b* and releasing the tab 330*b* out of the detent 332*a*. The cut out 336*b* provides the tab 330*b* room to move in the longitudinal axis and out of the detent 332*a*. Once the tab 330*b* is released the component 370 may be pulled forward along the spaced apart rails of both components 338*a*, 340*a* and 322*b*, 324*b* removing component 370 from component 360.

Component 380 may be decoupled from component 360 by inserting a removal tool (not shown) along the angled slope 334*a* and releasing the tab 330*a* out of the detent, similar to detent 332*a*, 332*b*, (not shown). The cut out 336*a* provides the tab 330*a* room to move in the longitudinal axis and out of the detent (not shown). Once the tab 330*a* is released the component 360 may be pulled forward along the spaced apart rails of both components 322*a*, 324*a* and 322*c*, 324*c* removing component 360 from component 380.

In some embodiments, the decoupling and removal of the tibial tray component 190, from at least one other component (e.g., component 360, 370, and/or 380) allows access to the internal engagement features of at least one other component 360, 370, 380. Removal of the tibial tray component 190, may be achieved with an impacting instrument(s) in a distal or caudal direction as will be understood by one of ordinary skill in the art. The internal engagement features of the components 360, 370, 380 may be spaced apart rails, such as the spaced apart rails 338*a*, 340*a* of component 360, and may be configured and arranged to engage a removal instrument (not shown). The removal instrument may engage the internal engagement features of components 360, 370, and/or 380, such as the spaced apart rails 338*a*, 340*a* of component 360, to facilitate removal. It is understood that the internal engagement features may also include holes, tabs, threads, and/or recesses to facilitate engagement with the removal instrument(s).

As best seen in FIGS. 30-33, stem components may include an extraction opening 342*a*, 342*b* in the body 302*a*, 302*b* configured to fit a separate tool, such as extraction tool 134, to allow for the decoupling and removal of at least one component, such as components 360, 370, and/or 380. In some embodiments, the extraction tool 134 may include a handle 136 disposed on a first end of the extraction tool 134 and an extraction mechanism 138 disposed on a second end of the extraction tool 134. The extraction mechanism 138, may in some embodiments, be a protrusion that extends at an angle from the shaft and adapted to fit inside of a recess 140*a*, 140*b* disposed inside of the extraction opening 342*a* 342*b* on body 302*a*, 302*b*. In some embodiments, the decoupling and removal of the stem components may include inserting the extraction tool 134 and extraction mechanism 138 into the extraction opening 342*a*, 342*b* and a recess 344*a*, 344*b* disposed on body 302*a*, 302*b*. Removal may then be facilitated by pulling away from (or in the posterior direction) the stem allowing the stem components to move along the spaced apart rails, such as spaced apart rails 338*a*, 340*a* and 322*b*, 324*b* of components 360 and 370 respectively.

In some embodiments, a system may include a first component, an engagement element, a biasing member, and a securing mechanism. The first component may have a first body extending from a first face to a second face. The engagement element may be disposed on the first face of the first body and may be configured to engage a second component. The biasing member may be disposed on the engagement element and may be configured to latch a second component to the first component. The securing mechanism may be configured to receive a locking mechanism at an angle with respect to a longitudinal axis. The locking mechanism may be adapted to interact with the biasing member.

In some embodiments, the first face on the first body may have a respective first edge and second edge.

In some embodiments, the securing mechanism may be configured to receive the locking mechanism at a perpendicular angle with respect to the longitudinal axis.

In some embodiments, the biasing member may be adapted to move in an up and a down direction.

In some embodiments, the engagement element may include a pair of spaced apart rails.

In some embodiments, the biasing member may include a clip.

In some embodiments, the locking mechanism may include a fastener configured to be received in an opening defined by the first body and adapted to interact with said biasing member. An interaction between the fastener and the biasing member may push the biasing member into a first position.

In some embodiments, the opening is at least partially threaded.

In some embodiments, the opening is at least partially tapered.

In some embodiments, the fastener may be a set screw configured to be received in the opening on the first body.

In some embodiments, the second component may include a second body extending from a first face to a second face. The second body may include rails on the first face of the second body. A detent may be disposed on a second face of the second body. The rails on the second body may be adapted to fit with the engagement element of the first component coupling the first and second components together.

In some embodiments, the biasing member, when pushed into the first positon by the fastener, may be adapted to lock the coupling of the first and second components together.

In some embodiments, the first component may include an angled slope on the first body sized to allow a removal tool access to the biasing member to decouple the first component from the second component.

In some embodiments, a system may include a tray configured to be coupled to the second component and an articular surface configured to be coupled to the tray.

In some embodiments, the first and second components may be formed using an additive manufacturing process.

In some embodiments, the bodies of the first and second components further comprise an extraction opening and a recess adapted to fit an extraction tool and extraction mechanism to facilitate the removal of the first and second components.

In some embodiments, a method may include coupling a first component to a second component by aligning a pair of rails on the first component to a pair of rails on the second component sliding the second component in a posterior direction to engage the pair of rails of the second component with the pair of rails on the first component.

In some embodiments, a method may include installing a locking mechanism into a securing mechanism disposed on an outer surface of the first component at an angle with respect to a longitudinal axis of the first component. The locking mechanism may be adapted to push a biasing member into a first position.

In some embodiments, the first and second components may be components of a stem.

In some embodiments, a method may include inserting the stem into an intramedullary canal formed in a tibia.

In some embodiments, a method may include coupling a tibial tray component to the stem.

In some embodiments, a method may include coupling the second component to another component.

In some embodiments, a respective body of each of the first and second components may include a detent on a respective second face.

In some embodiments, the biasing member may include a fastener configured to lock the first and second components together.

In some embodiments, a method may include decoupling a first component from a second component. The first and second components may both include a respective body. The respective bodies may include respective spaced apart rails of the first and second component. The decoupling may include unlocking the first and second components by uninstalling a locking mechanism from a securing mechanism disposed, at an angle with respect to a longitudinal axis of the first component on an outer surface of the first component. The removal of the locking mechanism may move a biasing member into a second position. The decoupling may include moving the first and second components apart by sliding the respective spaced apart rails away from each other by pulling an extraction tool handle in a posterior direction.

In some embodiments, a system may include a first component, a pair of rails, and a biasing member. The first component may include a first body extending from a first face to a second face. The pair of rails may be disposed on the first face of the first body. The pair of rails may be configured to engage a second component. The biasing member may be disposed on the first face of the first body and may be configured to latch the first and second component together.

In some embodiments, the first body may include an angled slope on the first face of the first body and may include a detent on the second face of the first body configured to receive a tab.

In some embodiments, the biasing member may include a tab and a cut out to allow movement of the tab.

In some embodiments, the cut out may be circular in shape.

In some embodiments, the second component may include a second body and a pair of rails. The second body may extend from a first face to a second face. The pair of rails disposed on the first face of the second body. The rails may be configured to slide along the rails of the first component coupling the first and second components together.

In some embodiments, the second body may include an angled slope, disposed on the first face of the second body, and may include a detent on the second face of the second body, configured to receive a tab.

In some embodiments, the second component may include a second biasing member disposed on the first face of the second component. The second biasing member may include a second tab on a top side of the second biasing member adapted to lock the second component and may include at least one other component together.

In some embodiments, the second biasing member may include a second cut out on a bottom side of the second biasing member allowing movement of the second biasing member.

In some embodiments, a system may include a removal tool configured to release the second tab decoupling the first and second components.

In some embodiments, a system may include a tray configured to be coupled to the second component and may include an articular surface configured to be coupled to the tray.

In some embodiments, the first and second components may be formed using an additive manufacturing process.

In some embodiments, a method may include coupling a first component and a second component together by aligning a respective pair of rails of the first and second components and locking the first and second components together with an engagement element disposed on a first face of the second component. The engagement element may include a tab, a cut out, an angled slope, and a ledge. The tab may be configured to fit inside of a detent. The cut out on the bottom side of the tab may be configured to allow the tab to bend. The angled slope may be adapted to allow a removal tool access. The ledge may be on the first end of the tab. The ledge may be adapted to lock inside of a detent on a bottom end of the first component.

In some embodiments, a method may include coupling the second component to another component.

In some embodiments, the first and second components may be components of a stem.

In some embodiments, a method may include inserting the stem into an intramedullary canal formed in a tibia.

In some embodiments, a method may include coupling a tibial tray component to the stem.

In some embodiments, a method may include decoupling a first component from a second component. The first and second components may include a respective body. The respective bodies may include respective spaced apart rails. The decoupling may include sliding a removal tool along an angled slope on the body of the second component. The removal tool may be adapted to engage a tab on the second component and may remove the tab from a detent on a second face of the first component. If the tab is removed from the detent, moving the respective spaced apart rails of the first and second component apart by pulling an extraction tool handle in a posterior direction completing the decoupling.

Although the components, systems, kits, and methods have been described in terms of exemplary embodiments, they are not limited thereto. Rather, the appended claims should be construed broadly, to include other variants and embodiments of the components, systems, kits, and methods, which may be made by those skilled in the art without departing from the scope and range of equivalents.

What is claimed is:

1. A system, comprising:

a first component having:

a first body extending from a first face to a second face;

an engagement element disposed on the first face of the first body and configured to engage a second component;

a biasing member disposed on the engagement element and configured to latch the second component to the first component; and an at least partially threaded opening defined by the first body and configured to receive a fastener of a locking mechanism at an angle with respect to a longitudinal axis, the fastener being adapted to interact with the biasing member, and wherein an interaction between the fastener and the biasing member pushes the biasing member into a first position.

2. The system of claim 1, wherein the first face on the first body has a respective first edge and second edge.

3. The system of claim 1, wherein the securing mechanism is configured to receive the locking mechanism at a perpendicular angle with respect to the longitudinal axis.

4. The system of claim 1, wherein the biasing member is adapted to move in an up and a down direction.

5. The system of claim 1, wherein the engagement element includes a pair of spaced apart rails.

6. The system of claim 1, wherein the biasing member includes a clip.

7. The system of claim 1, wherein the opening is at least partially tapered.

8. The system of claim 1, wherein the second component further includes a second body extending from a first face to a second face, the second body including rails on the first face of the second body, and a detent disposed on the second face of the second body, wherein the rails on the second body are adapted fit with the engagement element of the first component coupling the first and second components together.

9. The system of claim 8, wherein the biasing member, when pushed into the first positon by the fastener, is adapted to lock the coupling of the first and second components together.

10. The system of claim 8, further comprising:

a tray configured to be coupled to the second component; and an articular surface configured to be coupled to the tray.

11. The system of claim 8, wherein the first and second components are formed using an additive manufacturing process.

12. A system, comprising:

a first component having: a first body extending from a first face to a second face;

an engagement element disposed on the first face of the first body and configured to engage a second component;

a biasing member disposed on the engagement element and configured to latch a second component to the first component; and an opening defined by the first body and configured to receive a set screw of a locking mechanism at an angle with respect to a longitudinal axis, wherein, the set screw is adapted to interact with the biasing member, and further wherein an interaction between the set screw and the biasing member pushes the biasing member into a first position.

* * * * *